US008105572B2

(12) United States Patent
Condos et al.

(10) Patent No.: US 8,105,572 B2
(45) Date of Patent: *Jan. 31, 2012

(54) METHOD OF TREATING TUBERCULOSIS WITH INTERFERONS

(75) Inventors: Rany Condos, Bechurst, NY (US); Gerald Smaldone, Setauket, NY (US)

(73) Assignees: New York University, New York, NY (US); Research Foundation of State University of New York, Albany, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/589,228

(22) Filed: Oct. 20, 2009

(65) Prior Publication Data

US 2010/0098660 A1 Apr. 22, 2010

Related U.S. Application Data

(63) Continuation-in-part of application No. 12/154,158, filed on May 19, 2008.

(60) Provisional application No. 60/930,881, filed on May 18, 2007, provisional application No. 61/063,123, filed on Jan. 30, 2008.

(51) Int. Cl.
*A61K 38/00* (2006.01)
*A61K 38/21* (2006.01)
*C07K 14/00* (2006.01)

(52) U.S. Cl. .......... 424/85.4; 514/2.3; 514/2.4; 514/1.5; 424/85.5; 530/351

(58) Field of Classification Search ........................ None
See application file for complete search history.

(56) References Cited

U.S. PATENT DOCUMENTS

| | | | | |
|---|---|---|---|---|
| 5,284,656 | A | 2/1994 | Platz et al. | |
| 6,964,761 | B1 * | 11/2005 | Condos et al. | 424/85.5 |
| 2001/0043906 | A1 * | 11/2001 | Vlasselaer et al. | 424/43 |
| 2005/0220763 | A1 | 10/2005 | Condos et al. | |
| 2007/0065367 | A1 | 3/2007 | Condos et al. | |
| 2009/0123422 | A1 | 5/2009 | Condos et al. | |

FOREIGN PATENT DOCUMENTS

WO 2004/112691 A2 12/2004

OTHER PUBLICATIONS

Maartens, et al. (2007) Lancet 370: 2030-2043.
Young, et al. (2008) J Clin Invest 118: 1255-1265.
Tuberculosis Trials Consortium (2002) Lancet 360: 528-534.
Condos, et al. (2003) Infect Immun 71: 2058-2064.
Tramontana, et al. (1995) Mol Med 1: 384-397.
Grassi, et al. (2006) Clin Immunol 121: 100-107.
Bai, et al. (2004) Tuberculosis 84: 375-385.
Bonecini-Almeida, et al. (2004) Infect Immun 72: 2628-2634.
Dheda, et al. (2007) Tuberculosis 87: 237-241.
Gold, et al. (2004) Infect Immun 72: 645-650.
MacMicking, et al. (2003) Science 02: 654-659.
Marchant, et al. (2001) Am J Respir Cell Mol Biol 24:187-194.
Toossi (2000) Archivum Immunologiae et Therapiae Experimentalis 48: 513-519.
Kaufmann (2002) Ann Rheum Dis 61 Suppl 2: ii54-8.
Houben et al. (2006) Curr Opin Microbiol 9 (1): 76-85.
Flynn et al., J Exp Med 1993; 178:2249-2254.
Seneviratne et al., Thorax 2007; 62:97-99.
Dorman et al., Lancet 2004; 364:2113-2121.
Kamijo et al., J exp med 1993; 178:1435-1440.
Hirsch et al., J Infect Dis 1999; 180:2069-73.
Hougardy et al., Am J Respir Crit Care Med 2007; 176:409-416.
Law et al., Am J. Respir Crit Care Med 1996; 153:1377-1384.
Condos et al., Am J. rispir Crit Care Med 1998; 157:729-735.
Raviglione, et al. (2005) Harrison's Principle's of Internal Medicine, 953.
Parrish et al., (1998) Trends Microbiol 6 (3): 107-12.
Onyebujoh et al., World Health Organization Disease Watch: Focus: Tuberulosis. Dec. 2004.
O'Brien R (1994) Semin Respir Infect 9 (2): 104-12.
(2003) MMWR Morb Mortal Wkly Rep 52 (31): 735-9.
(2006) MMWR Morb Mortral Wkly Rep 55 (11): 301-5.
Bemiller, et al. (1995) Blood Cells Mol Dis 21(3): 239-47.
Weening et al., (1995) Eur J Pediatr 154(4): 295-8.
Boguniewicz et al., (1995) J Allergy Clin Immunol 95(1) Pt 1:133-5.
Condos et al., (1997) lancet 349(9064): 1513-5.
Jaffe et al., J Clin Invest. 88, 297-302 (1991).
Ziesche et al., (1999) N. Eng. J. Med., 341, 1264-1269.
Doffinger et al., CLin Inf Dis (2004) 38:e10-e14.
Holland et al., N Engl J Med (1994) 330: 1348-55.
Colsky et al., Arch Dermatol (1999) 135:125-127.
Raju et al., Infect Immun (2004) 72: 1275-1283.
Nicholson et al., J Exp Med (1996) 183: 2293-2302.
Suarez-Mendez et al., BMC Infect Dis (2004) 4: 44.
Giosue et al., Am J. Respir Crit Care Med (1998) 158: 1156-1162.
Palmero et al., Int J Tuberc Lung Dis (1999) 3:214-218.
Johnson et al., AM J Respir Crit Care Med (2003) 168:185-191.
Zhang et al., J Clin Invest (1995) 95:586-592.
Martineau et al., J Clin Invest (2007) 117: 1988-1994.
Schwander et al., J Infect Dis (1996) 173: 1267-1272.
Alonso et al., Proc Natl Acad Sci (2007) 104: 6031-6036.
Fuller et al., Infect Immun (2003) 71:7023-7034.
Strieter et al., Am J Respir Crit Care Med (2004) 170: 133-140.
Lienhardt et al., Eur J Immunol (2002) 32: 1605-1613.
Robinson et al., Am J Respir Crit Care Med (1994) 149: 989-993.
Yamada et al., Am J Respir Crit Care Med (2000) 161:1786-1789.
Condos et al., Chest (2004) 125: 2146-2155.

(Continued)

*Primary Examiner* — Christine J Saoud
*Assistant Examiner* — Jegatheesan Seharaseyon
(74) *Attorney, Agent, or Firm* — Klauber & Jackson LLC

(57) ABSTRACT

A method of treating tuberculosis comprising administering an aerosolized interferon such as interferon α, interferon β or interferon γ in a therapeutically effective amount is provided herein. Further, a method of reducing the infectivity of tuberculosis or reducing the number of infectious organisms present in the lungs of a patient suffering from tuberculosis comprising administering an aerosolized interferon such as interferon α, interferon β or interferon γ in a therapeutically effective amount is provided herein. Also, pharmaceutical compositions of one or more aerosolized interferon(s) are provided.

23 Claims, 20 Drawing Sheets

OTHER PUBLICATIONS

Klingler et al., Infect Immun (1997) 5:5272-5278.
Van der Wel et al., Cell (2007) 129: 1287-1298.
Gutierrez et al., Cell (2004) 119: 753-766.
Vilcek et al., (1994) Int Arch Allergy Immunol 104(4): 311-6.
Young et al., (1995) J Leukoc Biol 58(4): 373-81.
Pine, R. (1992) J Virol 66(7): 4470-8.
Pine et al., (1994) Embo J 13(1): 158-67.
Pine et al., (1990) Mol Cell Biol 10(6): 2448-57.
Harada et al., (1994) Mol Cell Biol 14(2): 1500-9.
Johnson et al., (1994) Mol Cell Biol 14(2): 1322-32.
White et al., (1996) Immunity 5(4): 365-76.
Nunokawa et al., (1994) Biochem Biophys Res Commun 200(2): 802-7.
Darnell (1996) Recent Prog Horm Res 51:391-403.
Ivashkiv, L. B. (1995) Immunity 3(1): 1-4.
Adjei et al., Pharmaceutical Research, vol. 7, No. 6, pp. 565-569 (1990).
Adjei et al., International Journal of Pharmaceutics, 63:135-144 (1990).
Braquet et al., Journal of Cardiovascular Pharmacology, vol. 13, suppl. 5, s. 143-146 (1989).
Hubbard et al., Annals of Internal Medicine, Vol. III, No. 3, pp. 206-212(1989).
Smith et al., J. Clin. Invest., vol. 84, pp. 1145-1146 (1989).
Oswein et al., "Aerosolization of Proteins", Proceedings of Symposium on Respiratory Drug Delivery II, Keystone, Colo., Mar. 1990.
Kanazawa, et al., Chest, (2003) 123:2: 600-603.
Raghu, et al., New England Journal of Medicine (2004) 350:2: 125-133.
The Internatonal Chronic Granulomatous Disease Cooperative Study Group, N Engl J Med (1991) 324(8): 509-16.

* cited by examiner

Figure 2 (filled bar indicates aerosol generation)

SLOW & DEEP
following 3 breaths of
Test aerosol (albuterol)

TIDAL BREATHING
following 20 breaths of
Test aerosol (albuterol)

Conversion of sputum cultures over time

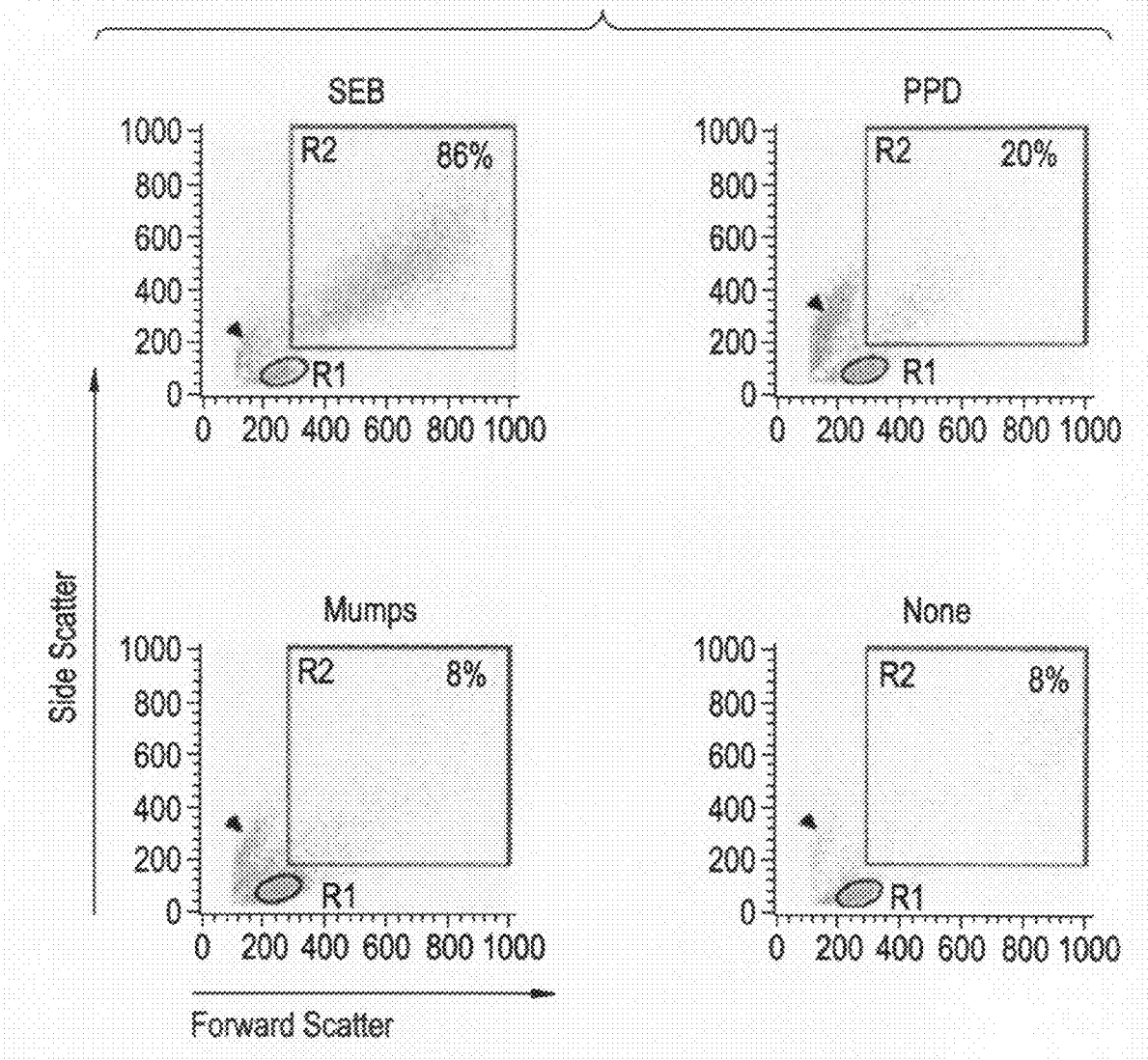

METHOD OF TREATING TUBERCULOSIS WITH INTERFERONS

RELATED APPLICATIONS

The present application is a continuation in part of U.S. Ser. No. 12/154,158, filed May 19, 2008 which in turn claims the benefit under 35 U.S.C. §119 of U.S. Provisional Application Ser. No. 60/930,881, filed May 18, 2007 and U.S. Provisional Application Ser. No. 61/063,123, filed Jan. 30, 2008, the contents of which applications are hereby incorporated by reference in their entireties.

GOVERNMENT SUPPORT

Some research leading to the present invention was supported in part by NIH research Grant No. 5 R01 HL056832. Accordingly, the United States Government has certain rights in the invention.

FIELD OF THE INVENTION

This invention relates to methods of treating pulmonary diseases using aerosol interferons, formulations of one or more interferons for aerosol delivery and methods for determining aerosol deposition.

BACKGROUND

Tuberculosis is a common and deadly infectious disease that is caused by mycobacteria, primarily *Mycobacterium tuberculosis*. Tuberculosis most commonly affects the lungs but can also affect the central nervous system, the lymphatic system, the circulatory system, the genitourinary system, bones, joints and even the skin. Other mycobacteria such as *Mycobacterium bovis, Mycobacterium africanum, Mycobacterium canetti* and *Mycobacterium microti* can also cause tuberculosis, but these species do not usually infect healthy adults. Raviglione, et al. (2005). Harrison's Principle's of Internal Medicine, 953.

Over one-third of the world's population now has the tuberculosis bacterium in their bodies and new infections are occurring at a rate of one per second. World Health Organization (WHO). Tuberculosis Fact sheet No. 104—Global and regional incidence. March 2006, Not everyone who is infected develops the disease and asymptomatic latent tuberculosis infection is most common. However, one in ten latent infections will progress to active tuberculosis disease which, if left untreated, kills more than half of its victims. In 2004, 14.6 million people had active tuberculosis and there were 8.9 million new cases and 1.7 million deaths, mostly in developing countries. Drug-resistant strains of tuberculosis have emerged and are spreading (in 2000-2004, 20% of cases were resistant to standard treatments and 2% were also resistant to second-line drugs). "Emergence of *Mycobacterium tuberculosis* with extensive resistance to second-line drugs—worldwide, 2000-2004". MMWR Morb Mortal Wkly Rep 55 (11): 301-5.

In the patients where tuberculosis becomes an active disease, 75% of these cases affect the lungs, where the disease is called pulmonary tuberculosis. Symptoms include a productive, prolonged cough of more than three weeks duration, chest pain and coughing up blood. Systemic symptoms include fever, chills, night sweats, appetite loss, weight loss and paling, and those afflicted are often easily fatigued. When the infection spreads out of the lungs, extrapulmonary sites include the pleura, central nervous system in meningitis, lymphatic system in scrofula of the neck, genitourinary system in urogenital tuberculosis, and bones and joints in Pott's disease of the spine. An especially serious form is disseminated or miliary tuberculosis. Extrapulmonary forms are more common in immunosuppressed persons and in young children. Infectious pulmonary tuberculosis may co-exist with extrapulmonary tuberculosis, which is not contagious. Centers for Disease Control and Prevention (CDC), Division of Tuberculosis Elimination. Core Curriculum on Tuberculosis: What the Clinician Should Know. 4th edition (2000). Updated August 2003.

The primary cause of tuberculosis, *Mycobacterium tuberculosis* (MTB), is a slow-growing aerobic bacterium. Microbiology 150 (Pt 5): 1413-26. MTB is identified microscopically by its staining characteristics: it retains certain stains after being treated with acidic solution, and is thus classified as an "acid-fast *bacillus*" or AFB. Madison (2001) Biotech Histochem 76 (3): 119-25. In the most common staining technique, the Ziehl-Neelsen stain, AFB are stained a bright red which stands out clearly against a blue background. Acid-fast bacilli can also be visualized by fluorescent microscopy, and by an auramine-rhodamine stain.

Tuberculosis is spread by aerosol droplets expelled by people with the active disease of the lungs. Transmission can only occur from people with active—not latent—TB disease. The probability of transmission from one person to another depends upon the quantity of the infectious droplets expelled by the patient, the effectiveness of ventilation, the duration of exposure, and the virulence of the *Mycobacterium tuberculosis* strain. Centers for Disease Control and Prevention (CDC), Division of Tuberculosis Elimination. Core Curriculum on Tuberculosis: What the Clinician Should Know. 4th edition (2000). The chain of transmission can therefore be broken by isolating patients with active disease and starting effective anti-tuberculous therapy.

Tuberculosis is classified as one of the granulomatous inflammatory conditions. Macrophages, T lymphocytes, B lymphocytes and fibroblasts are among the cells that aggregate to form a granuloma, with lymphocytes surrounding the infected macrophages. The granuloma functions not only to prevent dissemination of the mycobacteria, but also provides a local environment for communication of cells of the immune system. Within the granuloma, T lymphocytes (CD4+) secrete cytokines such as interferon gamma, which activates macrophages to destroy the bacteria with which they are infected. Kaufmann (2002) Ann Rheum Dis 61 Suppl 2: ii54-8. T lymphocytes (CD8+) can also directly kill infected cells. Houben et al. (2006) Curr Opin Microbiol 9 (1): 76-85.

HIV-1-infection markedly reduces host defense and increases disease progression in the absence of DOTS, highlighting the role of cellular immunity in controlling mycobacteria. Transgenic knockout models of mycobacteria-exposed mice demonstrated that interferon-γ and its signaling intermediates are critical to host defense (Flynn et al., *J Exp Med* 1993; 178:2249-2254; Kamijo et al., *J Exp Med* 1993; 178:1435-1440). In humans, mutational defects in the interferon-γ receptor, the cytokine IL-12, or antibodies to interferon-γ result in disseminated mycobacterial infection (Seneviratne et al., *Thorax* 2007; 62:97-99; Dorman et al., *Lancet* 2004; 364:2113-2121). Treatment of these patients with recombinant interferon-γ has been successful and safe.

Responses of whole blood PBMC to PPD and other mycobacterial antigens are reduced in active tuberculosis probably due to suppressor T cells (Tregs or Th17 cells) or cytokines, e.g. IL-10 or TGF-β (Hirsch et al., *J Infect Dis* 1999; 180: 2069-73; Hougardy et al., *Am J Respir Crit Care Med* 2007; 176: 409-416). Bronchoalveolar lavage (BAL) of patients with pulmonary tuberculosis has shown increases in interferon-γ and percent CD4+ cells compared to uninfected controls, but in advanced, cavitary tuberculosis or TB/HIV-1 coinfection these markers of effective immunity are reduced (Law et al., *Am J Respir Crit Care Med* 1996; 153:1377-1384; Condos et al., *Am J Respir Crit Care Med* 1998; 157:729-735).

Progression from tuberculosis infection to tuberculosis disease occurs when the tuberculosis bacilli overcome the immune system defenses and begin to multiply. In primary tuberculosis disease—1 to 5% of cases—this occurs soon after infection. However, in the majority of cases, a latent infection occurs that has no obvious symptoms. These dormant bacilli can produce tuberculosis in 2 to 23% of these latent cases, often many years after infection. Parrish et al., (1998) Trends Microbiol 6 (3): 107-12. The risk of reactivation increases with immunosuppression, such as that caused by infection with HIV. In patients co-infected with *M. tuberculosis* and HIV, the risk of reactivation increases to 10% per year. Onyebujoh et al. *World Health Organization Disease Watch: Focus: Tuberculosis*. December 2004.

Treatment for tuberculosis uses antibiotics to kill the bacteria. The two antibiotics most commonly used are rifampicin or rifampin and isoniazid. However, these treatments are more difficult than the short courses of antibiotics used to cure most bacterial infections as long periods of treatment (around 6 to 12 months) are needed to entirely eliminate mycobacteria from the body. Centers for Disease Control and Prevention (CDC), Division of Tuberculosis Elimination. Core Curriculum on Tuberculosis: What the Clinician Should Know. 4th edition (2000). Latent tuberculosis treatment usually uses a single antibiotic, while active tuberculosis disease is best treated with combinations of several antibiotics, to reduce the risk of the bacteria developing antibiotic resistance. O'Brien (1994) *Semin Respir Infect* 9 (2): 104-12. People with these latent infections are treated to prevent them from progressing to active tuberculosis disease later in life. However, treatment using Rifampin and Pyrazinamide is not risk-free. The Centers for Disease Control and Prevention (CDC) notified healthcare professionals of revised recommendations against the use of rifampin plus pyrazinamide for treatment of latent tuberculosis infection, due to high rates of hospitalization and death from liver injury associated with the combined use of these drugs. (2003) MMWR *Morb Mortal Wkly Rep* 52 (31): 735-9.

Drug resistant tuberculosis is transmitted in the same way as regular tuberculosis. Primary resistance occurs in persons who are infected with a resistant strain of tuberculosis. A patient with fully-susceptible tuberculosis develops secondary resistance (acquired resistance) during tuberculosis therapy because of inadequate treatment, not taking the prescribed regimen appropriately, or using low quality medication. O'Brien (1994) Semin Respir Infect 9 (2): 104-12. Drug-resistant tuberculosis is a public health issue in many developing countries, as treatment is longer and requires more expensive drugs. Multi-drug resistant tuberculosis (MDR—tuberculosis) is defined as resistance to the two most effective first line tuberculosis drugs: rifampicin and isoniazid. Extensively drug-resistant tuberculosis (XDR-TB) is also resistant to three or more of the six classes of second-line drugs. (2006) MMWR Morb Mortal Wkly Rep 55 (11): 301-5.

Clinical trials of recombinant interferon-γ (rIFN-γ) in humans are few. As of 1999, IFN-γ is indicated for the treatment of chronic granulomatous disease in which prolonged treatment (average duration 2.5 years) was associated with improvement in skin lesions, with minimal adverse events (fever, diarrhea, and flu-like illness) (*N Engl J Med* 324 (8): 509-16; Bemiller et al. (1995) *Blood Cells Mol Dis* 21(3): 239-47; Weening et al., (1995) *Eur J Pediatr* 154(4):295-8). Boguniewicz treated 5 patients with mild atopic asthma with escalating doses of aerosolized r IFN-γ (maximum dose of 500 mcg, total study dose of 2400 mcg) delivered over 20 days (Boguniewicz et al., (1995) *J Allergy Clin Immunol* 95(1) Pt 1: 133-5). All patients tolerated the nebulized r IFN-γ but there were no significant changes in the endpoints evaluated which included peak flow. InterMune sponsored several clinical trials to evaluate IFN-γ for infectious diseases. The MDR-TB clinical trial was entitled "A Phase II/III Study of the Safety and Efficacy of Inhaled Aerosolized Recombinant Interferon-γ 1 b in Patients with Pulmonary Multiple Drug Resistant Tuberculosis (MDR-TB) Who have Failed an Appropriate Three Month Treatment." This study enrolled 80 MDR-TB patients at several sites and randomized them to receive aerosol rIFN-γ (500 µg MWF) or placebo for at least 6 months in addition to second line therapy. This clinical trial was stopped prematurely due to lack of efficacy on sputum smears, M tb culture, or chest radiograph changes.

We administered nebulized rIFN-γ to 5 patients with persistent acid fast bacilli (AFB) smear and culture positive multiple-drug resistant tuberculosis (TB) (Condos et al., (1997) *Lancet* 349(9064): 1513-5). Patients received aerosol r IFN-γ, 500 mcg, 3 times weekly for 4 weeks (total study dose 6000 mcg). Therapy was tolerated well with minimal side effects. At the end of the 4 weeks, 4 of the 5 patients were sputum AFB-smear negative and the time to positive culture increased indicating a reduced organism load after treatment. Interestingly, in these reported and in additional patients, PEFR performed 1 hour after treatment improved by 6% (n=10).

Sputum culture positive at two months, cavitation on chest radiography, being underweight, and bilateral pulmonary involvement increases the risk of treatment failure and/or relapse (Tuberculosis Trials Consortium (2002) *Lancet* 360: 528-534. Responses of whole blood PBMC to PPD and other mycobacterial antigens are reduced in active tuberculosis probably due to suppressor T cells (Tregs) or cytokines, e.g. IL-10 or TGF-β (Hirsch, et al. (1999) *J Infect Dis* 180: 2069-2073; Hougardy, et al. (2007) *Am J Respir Crit Care Med* 176: 409-416.) Bronchoalveolar lavage (BAL) of patients with pulmonary tuberculosis has shown increases in inflammatory cytokines and percent CD4+ cells compared to uninfected controls, and in advanced, cavitary tuberculosis markers of effective immunity are reduced. Nitric oxide (NO) has been identified as a mechanism of mycobacterial killing, while mycobacteria can also be eliminated by autophagy, apoptosis, cytotoxic CD8+ cells, alpha defensins from neutrophils, and phagosomal-lysosomal rupture with subsequent cytosolic demise (Martineau, et al. (2007) *J Clin Invest* 117: 1988-1994; Van der Wel, et al. (2007) *Cell* 129: 1287-1298; Gutierez, et al. (2004) *Cell* 119: 753-766). However, mycobacteria have evolved virulence factors to persist in macrophages, possibly disrupting the interferon-γ signaling pathways.

Interferons are a family of naturally-occurring proteins that are produced by cells of the immune system. Three classes of interferons have been identified, alpha, beta and gamma. Each class has different effects though their activities overlap. Together, the interferons direct the immune system's attack on viruses, bacteria, tumors and other foreign substances that may invade the body. Once interferons have detected and attacked a foreign substance, they alter it by slowing, blocking, or changing its growth or function.

Interferon-γ is a pleiotropic cytokine that has specific immune-modulating effects, e.g. activation of macrophages, enhanced release of oxygen radicals, microbial killing, enhanced expression of MHC Class II molecules, anti-viral effects, induction of the inducible nitric oxide synthase gene and release of NO, chemotactic factors to recruit and activate immune effector cells, downregulation of transferrin receptors limiting microbial access to iron necessary for survival of intracellular pathogens, etc. Genetically engineered mice that lack interferon-γ or its receptor are extremely susceptible to mycobacterial infection.

Recombinant IFN-γ was administered to normal volunteers and cancer patients in the 1980s through intramuscular and subcutaneous routes. There was evidence of monocyte activation, e.g. release of oxidants. Jaffe et al. reported rIFNγ administration to 20 normal volunteers. (See, Jaffe et al., *J Clin Invest.* 88, 297-302 (1991)) First, they gave rIFN-γ 250 μg subcutaneously noting peak serum levels at 4 hours and a trough at 24 hours.

Several clinical trials were sponsored to evaluate IFN-γ for infectious diseases. The MDR-TB clinical trial, entitled "A Phase II/III Study of the Safety and Efficacy of Inhaled Aerosolized Recombinant Interferon-γ 1 b in Patients with Pulmonary Multiple Drug Resistant Tuberculosis (MDR-TB) Who have Failed an Appropriate Three Month Treatment," enrolled 80 MDR-TB patients at several sites (Cape Town, Port Elizabeth, Durban, Mexico) and randomized them to receive aerosol rIFN-γ (500 μg MWF) or placebo for at least 6 months in addition to second line therapy. This clinical trial was stopped prematurely due to lack of efficacy on sputum smears, Mtb culture, or chest radiograph changes.

Ziesche et al. gave rIFN-γ subcutaneously at a dose of 200 mg three times a week in addition to oral prednisone to 9/18 patients with idiopathic pulmonary fibrosis (IPF). See, Ziesche et al., (1999) *N. Eng. J. Med.,* 341, 1264-1269). The results of a subsequent phase 3 clinical trial of interferon γ-1b therapy for IPF were recently published. Although this was the first clinical trial of IPF that had an adequate sample size and was a randomized, prospective, double-blind, placebo-controlled study, no significant effect on markers of physiologic function, such as forced vital capacity, was observed. However, more deaths occurred in the placebo group, and survival was significantly better for a subset of patients who received interferon γ-1b therapy and had a forced vital capacity of 55% or greater and diffuse lung capacity for carbon monoxide of 35% or greater of the normal predicted values. The discordance between disease progression and survival in that study remains to be explained. One possibility is that interferon γ-1b therapy improves host defense against infection and diminishes the severity of lower respiratory tract infection when it complicates the clinical course of patients with IPF. This possibility is supported by the observation by Strieter et al. that the interferon-inducible CXC chemokine, I-TAC/CXCL11, which has antimicrobial properties, was significantly up-regulated in plasma and bronchoalveolar lavage (BAL) fluid in individuals who received interferon γ-1b compared to those who received placebo, whereas profibrogenic cytokines were generally not significantly altered by interferon γ-1b therapy over a 6-month treatment period. (See, Strieter et al., *Am J Respir Crit Care Med.* (2004). One possibility to explain the lackluster results is inadequate levels of drug delivered to the lung interstitium with current dosing strategies.

Interferon-γ is as essential for human host response to Mtb as it is in knockout mouse models. In a report of a patient with severe interferon-γ deficiency who developed disseminated TB, complete healing of skin, bone, pleural and renal lesions was achieved with subcutaneous IFN-γ1b three times a week at 50 μg for 34 weeks and 75 μg for 16 weeks (Seneviratne et al., *Thorax* (2007) 62:97-99). In another patient with autoimmune type I diabetes, primary hypothyroidism, and fatal disseminated Mtb infection, autoantibodies to interferon-γ that were capable of blocking in vitro responses to IFN-γ by peripheral blood mononuclear cells from normal donors were detected (Doffinger et al., *Clin Inf Dis* (2004) 38:e10-e14). Treatment of disseminated nontuberculous mycobacterial infection with subcutaneous IFN-γ has been clinically successful with correction of in vitro antigen-stimulated PBL responses (Holland et al., *N Engl J Med* (1994) 330: 1348-55). A patient with disseminated skin lesions due to M abscessus after chemotherapy for essential thrombocytosis had complete clearing of the skin after 7 months of subcutaneous IFN-γ, and a mid-course biopsy showed prominent MHC Class II immunostaining (Colsky et al., *Arch Dermatol* (1999) 135:125-127).

An open-label study of nebulized IFN-γ1b in 5 patients with MDR-TB showing clearing of the sputum after 1 month, as well as a second study in 10 TB patients showing enhanced IFN-γ signaling after one month of therapy with nebulized IFN-γ1b was previously reported (Condos et al., *Lancet* (1997) 349:1513-1515; Condos et al., *Infect Immun* (2003) 71: 2058-2064.). The IFN-γ inducible IP-10 was increased in BAL following nebulized IFN-γ1b but that nitric oxide synthase 1 (NOS2) was not increased further since over two-thirds of alveolar macrophages expressed this in active pulmonary TB at onset of treatment (Raju et al., *Infect Immun* (2004) 72: 1275-1283; Nicholson et al., *J Exp Med* (1996) 183: 2293-2302). Similar results were reported for 8 MDR-TB patients treated with intramuscular IFN-γ1b over a 6-month period (Suárez-Méndez et al., *BMC Infect Dis* (2004) 4:44). In a further study, nebulized interferon-α was given for 2 months as an adjunct in a randomized controlled clinical trial in 20 tuberculosis patients (Giosuè et al., *Am J Respir Grit Care Med* (1998) 158:1156-1162). Improvements in fever, *M tuberculosis* number in the sputum, abnormalities in CT-scans, and more significant decreases in BALF IL-1β, IL-6, and TNF-α were noted in the IFN-α group (Palmero et al., *Int J Tuberc Lung Dis* (1999) 3: 214-218). In a clinical trial of interleukin-2 adjunctive therapy performed in Uganda, 110 TB patients were randomized to IL-2 subcutaneously twice/day for the first 30 days in addition to DOTS versus DOTS alone. Seventeen percent versus 30% sputum conversion, respectively, was observed at 4 weeks (Johnson et al., *Am J Respir Crit Care Med* (2003) 168: 185-191). IL-2 might have upregulated CD4+CD25+ T regulatory cells, which could have down-regulated the immune system and impaired clearance of organisms.

The inflammatory response in the lung in TB may include an increase in neutrophils, particularly in radiographically abnormal areas (Law et al., *Am J Respir Crit Care Med* (1996) 153: 799-804). These involved segments have BAL cell supernatants and fluid that contain increased levels of IL-1β, IL-6, TNF-α, and IL-8, a chemokine for neutrophils (Law et al., *Am J Respir Crit Care Med* (1996) 153: 799-804; Zhang et al., *J Clin Invest* (1995) 95: 586-592). Mtb and its cell wall components lipoarabinomannan (LAM), lipomannan (LM), and phosphoinositolmannoside (PIM) stimulated IL-8 protein release and mRNA expression in vitro from alveolar macrophages (Zhang et al., *J Clin Invest* (1995) 95: 586-592). In a series of 30 pulmonary tuberculosis patients undergoing bronchoalveolar lavage, a sub-group had minimal disease with increased BAL lymphocytes with IFN-γ release, and a sub-group with cavitary tuberculosis had exaggerated percent and numbers of neutrophils with increased TNF-α and IL-1-β in BALF (Hougardy et al., *Am J Respir Crit Care Med* (2007) 176: 409-416). Neutrophils kill Mtb by oxidative and nonoxidative mechanisms probably by release of alpha defensins and bactericidal permeability increasing protein (Zhang et al., *J Clin Invest* (1995) 95: 586-592). Recently, human neutrophil peptides 1-3 were shown to kill Mtb and cathelicidin LL-37 and lipocalin 2 restricted growth of the organism, with the latter in an iron-dependent manner (Martineau et al., *J Clin Invest* (2007) 117: 1988-1994). Monocytes and macrophages are recruited to the site of Mtb inflammation by the release of the CC chemokines CCR2, monocyte chemotactic protein-1, and macrophage inflammatory protein-1α and -1β (Schwander et al., *J Infect Dis* (1996) 173: 1267-1272). Other mechanisms of Mtb killing may be modulated by IFN-γ include autophagy and ubiquitin in lysosomes (Alonso et al., *Proc Natl Acad Sci* (2007) 104: 6031-6036). IFN-γ-inducible chemokines CCXCL-9,-10, and -11 were increased in lung granulomas of cynmologus macaques infected with Mtb, and TNF-α, IFN-γ, and CD3+ cells were also abundant (Fuller et al., *Infect Immun* (2003) 71:7023-7034). CXCL-11 was also increased in BAL fluid from patients with idiopathic pulmonary fibrosis treated with subcutaneous IFN-γ1b (Strieter et al., *Am J Respir Crit Care Med* (2004) 170: 133-140).

Mtb usually produces an environment of immunological depression or stasis with reduced peripheral blood lymphocyte response to Mtb antigens that improves after treatment and becomes polarized to a Th1 profile of cytokines (Lienhardt et al., *Eur J Immunol* (2002) 32: 1605-1613). Treg or CD4+CD25+ cells are expanded in active tuberculosis and decline after treatment with concomitant return of T cell responses to PPD and release of IFN-γ (Condos et al., *Am J Respir Crit Care Med* (1998) 157:729-735). BAL lymphocytes and macrophages have increased mRNA transcripts for IFN-γ and IL-12 at the onset of active pulmonary tuberculosis (Robinson et al., *Am J Respir Crit Care Med* (1994) 149: 989-993). IL-18 synergizes with IL-12 in inducing IFN-γ, and correlates with fever and extent of radiographic tuberculous disease (Yamada et al., *Am J Respir Crit Care Med* (2000) 161: 1786-1789).

BRIEF SUMMARY OF THE INVENTION

In one aspect, the present invention features a method of treating a pulmonary disease in a subject suffering from a pulmonary disease, comprising administering an aerosolized interferon in a therapeutically effective amount. In some embodiments, the pulmonary disease is tuberculosis. In particularly preferred embodiments, the tuberculosis is resistant to multiple drugs (MDR-TB). In one embodiment, the improved symptoms of the pulmonary disease may be measured by one or more of a decrease in fever incidence or severity, a reduction in sputum production of 5, 10, 20, 25, 33, 50 or even 75% over a period of 2, 4, 6, 8, 10, 12, 16, or 24 weeks, a reduction in wheezing of 5, 10, 20, 25, 33, 50 or even 75% over a period of 2, 4, 6, 8, 10, 12, 16, or 24 weeks and a reduction in conversion of sputum cultures to test positive for tuberculosis pathogens. In other embodiments, the improved symptoms may include one or more of a reduction in tiredness, a reduction in the occurrence of night sweats of, for instance 10, 20, 25, 50 or even 75%, an improvement in appetite, a reduction in the frequency or duration of coughs, or a reduction in dyspnea. In other embodiments, the improved symptoms may be measured physiologically such as one or more of an increase in the number of lymphocytes present in biological samples obtained by bronchoalveolar lavage, a decrease in the number of neutrophils present in biological samples obtained by bronchoalveolar lavage, or a reduction in the amount of inflammatory cytokines present in biological samples obtained by bronchoalveolar lavage. The decreases or increases in each instance of neutrophils, lymphocytes or inflammatory cytokines may be on the order of 5%, 10%, 15%, 20%, 25%, 50%, 75% or even 100% or 200%. The interferon may be interferon α, interferon β or interferon γ.

In another embodiment, the subject suffering from the pulmonary disease, such as, for instance, tuberculosis, is unresponsive to treatment with one or more other therapeutics. Furthermore, in patients that are not sufficiently responsive to other therapeutics, it is a further aspect of the invention to combine treatment of these patients with an aerosolized interferon while maintaining treatment with one or more other therapeutic regimens, including but not limited to treatment with one or more antibiotic agents. Particularly useful antibiotics include isoniazid and rifampin.

In some embodiments, aerosolized interferon is administered in an amount so that interferon present in the lungs is elevated from a baseline level to a level that is believed to be therapeutic. The absolute amount of interferon that is administered in order to achieve an amount in the lungs that is believed to be therapeutic may vary according to such factors as the efficiency of delivery of the particular nebulizer used or the breathing patterns of the subject receiving the interferon therapy. In many embodiments, a sufficient amount of interferon is delivered to the lungs such that there is a 1.5×, 2×, 3×, 5×, 10×, 20×, 30×, 40×, 50× or even a 100× or more increase in interferon present in a bronchoalveolar lavage sample obtained from a subject after at least one treatment in comparison to the amount of interferon present in a bronchoalveolar lavage sample obtained from a subject before any interferon treatment. For instance, in some embodiments the baseline amount of interferon present in a bronchoalveolar lavage sample obtained from a subject before any interferon treatment may be about 10 μg/ml, 5 μg/ml, 1 μg/ml, 0.5 μg/ml or even less. In some embodiments, about one hour after a single dose treatment with interferon according to the present invention, the amount of interferon present in a bronchoalveolar lavage sample obtained from a subject may be about 15 μg/ml, 20 μg/ml, 25 μg/ml, 30 μg/ml, 40 μg/ml or even more.

In more specific embodiments, aerosolized interferon is administered in doses ranging from about 2 μg, 5 μg, 10 μg, 20 μg, 30 μg, 50 μg, 75 μg or 100 μg to about 750 μg or 1000 μg and may be given in a nebulizer once, twice, three or four times per week, preferably the dose may range from about 150 μg to 300 μg, 400 μg, 500 μg or even 600 μg. In another embodiment, a dose of 200 μg is given in a nebulizer three times per week. Lower doses may be given depending on the efficiency of the nebulizer or the type of inspiration breathing. When it is desired to treat patients with a combination of interferon-γ therapy and other treatment modalities, the aerosolized interferon-γ will be titrated to ensure no undesirable effects are experienced by these patients. Furthermore, when combination therapy is a consideration, the other agents may be delivered by a means in which they are considered to be the most effective. This may include intravenous, intramuscular, subcutaneous, or may be combined with IFN-γ and delivered as an aerosol.

In more specific embodiments, lower doses may be given depending on the efficiency of the nebulizer. When it is desired to treat patients with a combination of interferon-γ therapy and other treatment modalities, the aerosolized interferon-γ may be titrated to ensure no undesirable effects are experienced by these patients. Furthermore, when combination therapy is a consideration, the other agents may be delivered by a means in which they are considered to be the most effective. This may include intravenous, intramuscular, subcutaneous, or may be combined with INF-γ and delivered as an aerosol. In still other specific embodiments aerosolized interferon is administered in doses and for time periods and by devices such as nebulizers sufficient to provide INF-γ that may be measured in the bronchoalveolar lavage fluid (BAL) of patients. The INF-γ may be present in the BAL fluid in amounts of at least 10, 25, 50, 100, 150, 200, 250, 300, 500 or even 750 or more picograms/milliliter. Further, in other specific embodiments aerosolized interferon is administered in doses and for time periods sufficient to produce a measurable decrease in the level of IL-8 present in the bronchoalveolar lavage (BAL) fluid of a patient of for instance, 10%, 20%, 30%, 40%, 50% or more. In some instances, the level of IL-8 in the BAL of a patient suffering from a pulmonary disease may be reduced to an amount that is no more than 100%, 50%, 25%, or 10% more than the level of IL-8 in the BAL fluid of a normal control substantially free of a pulmonary disease. In yet additional specific embodiments aerosolized interferon is administered in doses and for time periods sufficient to produce a measurable increase in the level of TGF-β present in the bronchoalveolar lavage (BAL) fluid of a patient of from 5%, 10%, 15%, 20%, 25%, or even 50%, 60%, 75% or 100% or more. The TGF-β may be measured in the BAL fluid after treatment in some instances in amounts of about 0.25, 0.50, 0.75, 1.00, 1.25, 1.50, 1.75, or 2.00 picograms/milliliter or more. In many instances, the aerosolized interferon is administered preferably in a nebulizer from one to ten times per week, preferably about two, three, four or five times per week. In each of these instances the interferon may be administered for time periods of one week, two weeks, five weeks, ten weeks, twenty weeks, thirty weeks, forty weeks, 50 weeks, sixty weeks, seventy weeks or more to attain the desired IL-8, TGF-β, or INF-γ levels.

In some embodiments, the nebulizer is chosen so as to provide delivery of at least about 10%, 15%, 20%, 25%, 30%, 35%, 40%, 50%, 60% or even 75% or more of the interferon present in the nebulizer to the lung, some provided to the middle lobe of the lung. It is desirable that no more than about 5%, 10%, 15%, 20%, 25%, 30%, 35%, 40%, or 50% of the interferon administered be deposited in the gastrointestinal tract, such as, for instance, in the stomach. Moreover, it is desirable that no more than about 5%, 10%, 15%, 20%, 25%, 50% or 75% of the interferon remain undelivered to a patient in a drug delivery container of a nebulizer. Still further, it is desirable that no more than about 5%, 10%, 15%, 25%, 30%, 35%, 40%, or 50% of the interferon remain in the oropharynx or mouth of a patient.

In another aspect, the present invention features a method of reducing the infectivity of pulmonary disease in a subject suffering from a pulmonary disease, comprising administering an aerosolized interferon in a therapeutically effective amount. This aspect may also be described in some instances as a method of reducing the absolute or relative number or amount of infectious organisms present in the lungs or the concentration of infectious organisms present in a pulmonary tissue or fluid, such as, for instance sputum, of a patient suffering from a pulmonary disease, comprising administering an aerosolized interferon in a therapeutically effective amount. In some embodiments, the pulmonary disease is tuberculosis. In particularly preferred embodiments, the tuberculosis is resistant to multiple drugs (MDR-TB). In one embodiment, the improved symptoms of the pulmonary disease may be measured by one or more of a decrease in fever incidence or severity, a reduction in sputum production of 5, 10, 20, 25, 33, 50 or even 75% over a period of 2, 4, 6, 8, 10, 12, 16, or 24 weeks, a reduction in wheezing of 5, 10, 20, 25, 33, 50 or even 75% over a period of 2, 4, 6, 8, 10, 12, 16, or 24 weeks and a reduction in conversion of sputum cultures to test positive for tuberculosis pathogens. In other embodiments, the improved symptoms may include one or more of a reduction in tiredness, a reduction in the occurrence of night sweats of, for instance 10, 20, 25, 50 or even 75%, an improvement in appetite, a reduction in the frequency or duration of coughs, or a reduction in dyspnea. In other embodiments, the improved symptoms may be measured physiologically such as one or more of an increase in the number of lymphocytes present in biological samples obtained by bronchoalveolar lavage, a decrease in the number of neutrophils present in biological samples obtained by bronchoalveolar lavage, or a reduction in the amount of inflammatory cytokines present in biological samples obtained by bronchoalveolar lavage. The decreases or increases in each instance of neutrophils, lymphocytes or inflammatory cytokines may be on the order of 5%, 10%, 15%, 20%, 25%, 50%, 75% or even 100% or 200%. The interferon may be interferon α, interferon β or interferon γ.

In another embodiment, the subject suffering from the pulmonary disease, such as, for instance, tuberculosis, is unresponsive to treatment with one or more other therapeutics. Furthermore, in patients that are not sufficiently responsive to other therapeutics, it is a further aspect of the invention to combine treatment of these patients with an aerosolized interferon while maintaining treatment with one or more other therapeutic regimens, including but not limited to treatment with one or more antibiotic agents. Particularly useful antibiotics include isoniazid and rifampin.

In some embodiments, aerosolized interferon is administered in an amount so that interferon present in the lungs is elevated from a baseline level to a level that is believed to be therapeutic. The absolute amount of interferon that is administered in order to achieve an amount in the lungs that is believed to be therapeutic may vary according to such factors as the efficiency of delivery of the particular nebulizer used or the breathing patterns of the subject receiving the interferon therapy. In many embodiments, a sufficient amount of interferon is delivered to the lungs such that there is a 1.5×, 2×, 3×, 5×, 10×, 20×, 30×, 40×, 50× or even a 100× or more increase in interferon present in a bronchoalveolar lavage sample obtained from a subject after at least one treatment in comparison to the amount of interferon present in a bronchoalveolar lavage sample obtained from a subject before any interferon treatment. For instance, in some embodiments the baseline amount of interferon present in a bronchoalveolar lavage sample obtained from a subject before any interferon treatment may be about 10 pg/ml, 5 pg/ml, 1 pg/ml, 0.5 pg/ml or even less. In some embodiments, about one hour after a single dose treatment with interferon according to the present invention, the amount of interferon present in a bronchoalveolar lavage sample obtained from a subject may be about 15 pg/ml, 20 pg/ml, 25 pg/ml, 30 pg/ml, 40 pg/ml or even more.

In more specific embodiments, aerosolized interferon is administered in doses ranging from about 2 μg, 5 μg, 10 μg, 20 μg, 30 μg, 50 μg, 75 μg or 100 μg to about 750 μg or 1000 μg and may be given in a nebulizer once, twice, three or four or more times per week, preferably the dose may range from about 150 μg to 300 μg, 400 μg, 500 μg or even 600 μg or 700 μg or more. In another embodiment, a dose of 500 μg is given in a nebulizer three times per week. Lower doses may be given depending on the efficiency of the nebulizer or the type of inspiration breathing. When it is desired to treat patients with a combination of interferon-γ therapy and other treatment modalities, the aerosolized interferon-γ will be titrated to ensure no undesirable effects are experienced by these patients. Furthermore, when combination therapy is a consideration, the other agents may be delivered by a means in which they are considered to be the most effective. This may include intravenous, intramuscular, subcutaneous, or may be combined with IFN-γ and delivered as an aerosol.

In more specific embodiments, lower doses may be given depending on the efficiency of the nebulizer. When it is desired to treat patients with a combination of interferon-γ therapy and other treatment modalities, the aerosolized interferon-γ may be titrated to ensure no undesirable effects are experienced by these patients. Furthermore, when combination therapy is a consideration, the other agents may be delivered by a means in which they are considered to be the most effective. This may include intravenous, intramuscular, subcutaneous, or may be combined with INF-γ and delivered as an aerosol. In still other specific embodiments aerosolized interferon is administered in doses and for time periods and by devices such as nebulizers sufficient to provide INF-γ that may be measured in the bronchoalveolar lavage fluid (BAL) of patients. The INF-γ may be present in the BAL fluid in amounts of at least 10, 25, 50, 100, 150, 200, 250, 300, 500 or even 750 or more picograms/milliliter. Further, in other specific embodiments aerosolized interferon is administered in doses and for time periods sufficient to produce a measurable decrease in the level of IL-8 present in the bronchoalveolar lavage (BAL) fluid of a patient of for instance, 10%, 20%, 30%, 40%, 50% or more. In some instances, the level of IL-8 in the BAL of a patient suffering from a pulmonary disease may be reduced to an amount that is no more than 100%, 50%, 25%, or 10% more than the level of IL-8 in the BAL fluid of a normal control substantially free of a pulmonary disease. In yet additional specific embodiments aerosolized interferon is administered in doses and for time periods sufficient to produce a measurable increase in the level of TGF-β present in the bronchoalveolar lavage (BAL) fluid of a patient of from 5%, 10%, 15%, 20%, 25%, or even 50%, 60%, 75% or 100% or more. The TGF-β may be measured in the BAL fluid after treatment in some instances in amounts of about 0.25, 0.50, 0.75, 1.00, 1.25, 1.50, 1.75, or 2.00 picograms/milliliter or more. In many instances, the aerosolized interferon is administered preferably in a nebulizer from one to ten times per week, preferably about two, three, four or five times per week. In each of these instances the interferon may be administered for time periods of one week, two weeks, five weeks, ten weeks, twenty weeks, thirty weeks, forty weeks, 50 weeks, sixty weeks, seventy weeks or more to attain the desired IL-8, TGF-β, or INF-γ levels.

In some embodiments, the nebulizer is chosen so as to provide delivery of at least about 10%, 15%, 20%, 25%, 30%, 35%, 40%, 50%, 60% or even 75% or more of the interferon present in the nebulizer to the lung, some provided to the middle lobe of the lung. It is desirable that no more than about 5%, 10%, 15%, 20%, 25%, 30%, 35%, 40%, or 50% of the interferon administered be deposited in the gastrointestinal tract, such as, for instance, in the stomach. Moreover, it is desirable that no more than about 5%, 10%, 15%, 20%, 25%, 50% or 75% of the interferon remain undelivered to a patient in a drug delivery container of a nebulizer. Still further, it is desirable that no more than about 5%, 10%, 15%, 25%, 30%, 35%, 40%, or 50% of the interferon remain in the oropharynx or mouth of a patient.

BRIEF DESCRIPTION OF THE DRAWINGS

FIG. 2 describes a reduction in inspiratory flow and a greatly prolonged inspiratory time characteristic of a method of slow and deep inspiration as compared to tidal breathing.

DETAILED DESCRIPTION

Figure 1:
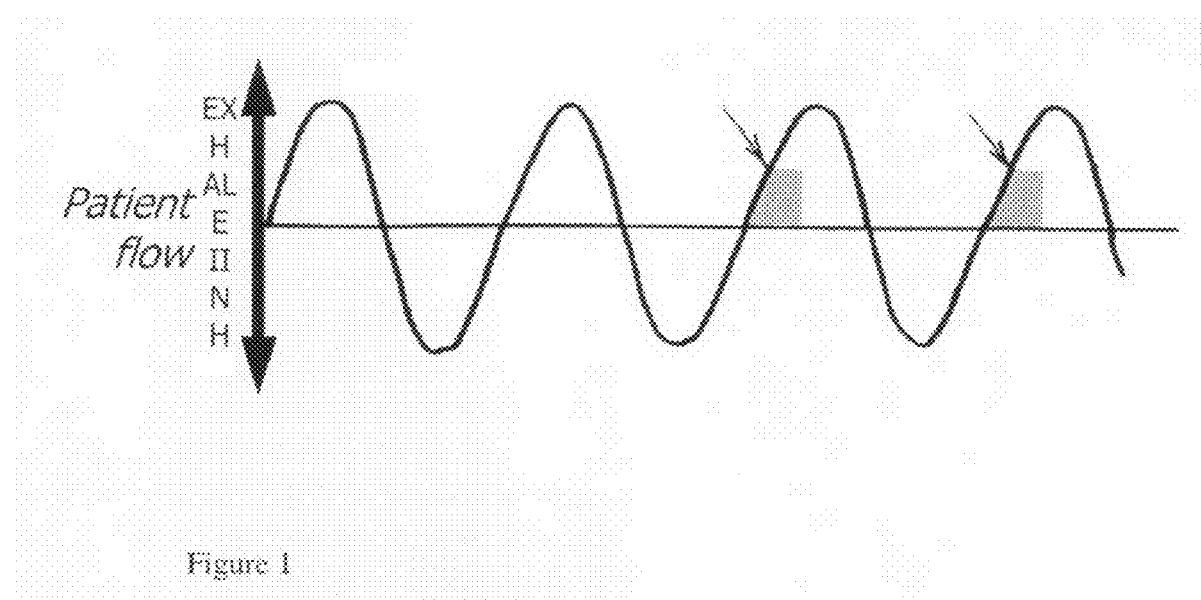
FIG. 1 describes a typical tidal breathing pattern.

Before the present methods and treatment methodology are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

As used in this specification and the appended claims, the singular forms "a", "an", and "the" include plural references unless the context clearly dictates otherwise. Thus for example, references to "the method" includes one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and described the methods and/or materials in connection with which the publications are cited.

DEFINITIONS

The phrase "unresponsive to treatment" means a patient population that is unresponsive to conventional prior art treatments.

Vital capacity (VC) means the total air that can be moved in and out of the lungs.

Fev1 means the forced expiratory volume of air in one second.

Fev1/FVC ratio means the ratio of forced expiratory volume in one second and forced vital capacity.

The term "pulmonary disease" refers to any pathology affecting at least in part the lungs or respiratory system. The term is meant to encompass both obstructive and non-obstructive conditions such as, for instance, asthma, emphysema, chronic obstructive pulmonary disease, pneumonia, tuberculosis, and fibrosis in all its forms including but not limited to idiopathic pulmonary fibrosis.

The term "obstructive pulmonary disease" refers to any pulmonary disease that results in reduction of airflow in or out of the respiratory system. The reduction in airflow relative to normal may be measured in total or over a finite time, for example, by FVC or FEV1.

The term "idiopathic pulmonary fibrosis" (IPF), synonymous with "cryptogenic fibrosing alveolitis" (CFA) is the clinical term for a major subgroup of the idiopathic interstitial pneumonias, and it describes a disease characterized by idiopathic progressive interstitial disease with a mean survival from the onset of dyspnea of 3 to 6 years. A diagnosis of idiopathic pulmonary fibrosis is made by identifying usual interstitial pneumonia (UIP) on lung biopsy. The histological pattern is characterized by heterogeneity that includes patchy chronic inflammation (alveolitis), progressive injury (small aggregates of proliferating myofibroblasts and fibroblasts, termed fibroblastic foci) and fibrosis (dense collagen and honeycomb change).

The term "asthma" refers to a common disease that involves inflammation (cellular injury) and narrowing of the airways leading to the lungs. Asthma occurs in children and adults. Childhood asthma may continue into adolescence and adulthood, but some adults who develop asthma did not have asthma when they were younger. Millions of people worldwide are affected by asthma, which has become more common in recent years.

The term "tuberculosis" refers to a common infectious disease caused by mycobacteria, primarily *Mycobacterium tuberculosis*. Tuberculosis most commonly affects the lungs but can also affect the central nervous system, the lymphatic system, the circulatory system, the genitourinary system, bones, joints and even the skin. Other mycobacteria such as *Mycobacterium bovis, Mycobacterium africanum, Mycobacterium canetti* and *Mycobacterium microti* can also cause tuberculosis, but these species do not usually infect healthy adults.

By "slow and deep breathing" is meant any breathing pattern wherein the time of inspiration is longer than the time of expiration. Such a pattern features a duty cycle (time of inspiration/total time of breath) of greater than 0.5. During normal tidal breathing the duty cycle is always less than or near 0.5. That is, the time of inspiration is always less than the time for expiration. In disease states, the duty cycle decreases in obstructive disease and for restrictive disorders it is likely to be still less than 0.5. "Slow and deep" breathing may feature an I/E ratio, time of inspiration relative to expiration of greater that 1, and in some instances the ratio may approach 8 or 9 thereby yielding a duty cycle of 0.8 or 0.9

By "infectivity" is meant the relative likelihood of an uninfected individual becoming infected upon contact or close encounter with an infected individual. "Infectivity" may be proportional to the relative or absolute numbers of infectious organisms present in the infected individual, or in the airways or lungs of an infected individual.

By "infectious organism" is meant the biological organism predominantly believed to be the putative agent causing a disease, disease process or constellation of clinical symptoms in another biological organism, such as, for instance, a human.

Five multiple-drug resistant tuberculosis patients were treated with nebulized IFN-γ1b while continuing their failing second-line regimens at a dose of 500 μg three times weekly for four weeks (Condos et al., *Lancet* (1997) 349:1513-1515). In all five patients, the sputum converted to negative, symptoms improved, and chest radiographs improved. In order to investigate the mechanisms of these responses, we used nebulized IFN-γ1b in eleven drug-sensitive tuberculosis patients, and found an increase in signaling molecules STAT-1, IRF-1 and IRF-9 (Condos et al., *Infect Immun* (2003) 71: 2058-2064). We observed widespread distribution of the nebulized drug (Condos et al., *Chest* (2004) 125: 2146-2155). In addition, nebulized IFN-γ 1b induced IP-10 downstream from these signaling molecules, but not inducible nitric oxide synthase (iNOS) (Raju et al., *Infect Immun* (2004) 72: 1275-1283). NO has been identified as a mechanism of mycobacterial killing, while mycobacteria can also be eliminated by autophagy, apoptosis, cytotoxic CD8+ cells, alpha defensins from neutrophils, and phagosomal-lysosomal rupture with subsequent cytosolic demise (Klingler et al., *Infect Immun* (1997) 5:5272-5278; Martineau et al., *J Clin Invest* (2007) 117: 1988-1994; Van der Wel et al., *Cell* (2007) 129: 1287-1298; Gutierrez et al., *Cell* (2004) 119: 753-766). However, mycobacteria have evolved virulence factors to persist in macrophages, possibly disrupting the interferon-γ signaling pathways. Therefore, to determine if IFN-γ1b could augment the host response, we conducted a 4-month randomized, controlled clinical trial with IFN-γ1b at 200 μg/day for three days/week with three arms: nebulized IFN-γ1b or subcutaneous IFN-γ1b with DOTS versus DOTS alone. We followed these for smear and culture conversion, clinical signs, immunological parameters and cytokines released by cells recovered by bronchoalveolar lavage.

A randomized, controlled clinical trial of directly observed therapy (DOTS) versus DOTS supplemented with nebulized or subcutaneously administered interferon-γ1b over 4 months to patients with cavitary pulmonary tuberculosis was performed. Bronchoalveolar lavage and blood were sampled at 0 and 4 months. All study subjects had sputum smears and cultures that were positive for *Mycobacterium tuberculosis* that was sensitive to at least 3 of 4 drugs.

96 cavitary tuberculosis patients were enrolled, and 89 met inclusion criteria. There was a significant ($p<0.05$) difference in the rate of clearance of Mtb from the sputum smear at 4 weeks for the nebulized interferon-γ1b adjuvant group compared to DOTS alone or DOTS with subcutaneous interferon-γ1b. In addition, there was significant ($p<0.05$) reduction in the prevalence of fever, wheeze, and night sweats at 4 weeks among patients receiving interferon-γ1b versus DOTS. There was a significant decline in levels of inflammatory cytokines IL-1β, IL-6, IL-8, and IL-10 in 24-hour BAL supernatants only in the nebulized interferon-γ1b group from baseline to week 16. Both interferon-γ1b groups had a significant increase in blood lymphocyte response to PPD at 4 weeks. Interferon-γ1b adjuvant therapy plus DOTS in cavitary pulmonary tuberculosis improves clearance of Mtb from the sputum, improve constitutional symptoms, and reduce inflammatory cytokines at the site of disease.

Interferon-γ Treatment of Tuberculosis

Bilateral cavitary tuberculosis and/or a persistently positive acid fast sputum smear at 2 months of therapy are both risk factors for treatment failure and/or relapse in tuberculosis patients. The extent of pulmonary disease (bilateral and cavitary) and the initial sputum response to four drug initiation phase therapy have a major impact on risk of relapse. Different strategies are required for managing these special risk patients. We investigated the effects of additive immunotherapy with recombinant gamma interferon (rIFN-γ) via subcutaneous injection and the novel aerosol delivery route.

An intact Type 2 interferon system is critical for an effective response to mycobacterial infections. The present protocol demonstrates an accelerated healing process in patients who demonstrate unsatisfactory response to traditional therapy for tuberculosis following exogenous recombinant interferon therapy. Aerosolized rIFN-γ has previously been shown to induce signal transduction in BAL cells and is a well tolerated delivery route. Subcutaneous injection results in peripheral monocyte activation and improved early clinical outcome in small groups of patients with both non-tuberculous (NTM) and tuberculous mycobacterial infection.

The mechanism of action of rIFN-γ in providing therapy for tuberculosis patients is thought to be through of the host TH1 immune response and macrophage activation. rIFN-γ provides in many instances a decrease in time to sputum conversion, prolongs time to mycobacterial detection in sputum culture, accelerates chest cavity closure by promoting healing thereby preventing parenchymal fibrosis, and provides earlier improvement in clinical parameters.

We conducted a randomised control trial at two recruitment sites, one in New York and one in Cape Town, South Africa. 100 patients were enrolled. For patients randomized to either of the treatment arms, recombinant interferon gamma (AC-TIMMUNE®, InterMune, Inc, Brisbane, Calif.) was delivered 3 times weekly either via the high efficiency AERO-ECLIPSE® nebuliser (Trudell Medical International, Canada) at a dose of 200 mcg or via subcutaneous injection at the equivalent 200 mcg dose strength. Immunotherapy dosing continued for a 16 week period with strict DOTS adherence monitoring.

Intention to treat analysis was performed on 100 subjects. While cough and improvement in appetite failed to show a significant improvement in the treatment groups versus standard treatment (DOTS), there were significant improvements seen in fever, p=0.04 at 12 weeks in combined rIFN treated patients versus standard treatment (DOTS) alone and in wheeze, p=0.03 at 4 weeks in combined rIFN treated versus standard treatment (DOTS) alone. Sputum conversion rates were better at 4 weeks in the Aerosol gamma treated group compared to standard treatment (DOTS) alone or standard treatment (DOTS) plus subcutaneous rIFN, p=0.05.

Five multiple-drug resistant tuberculosis patients were treated with nebulized rIFN-γ1b while continuing their failing second-line regimens at a dose of 500 μg three times weekly for four weeks (Condos, et al (1997) Lancet 349: 1513-1515). In all five patients, the sputum converted to negative, and symptoms improved. Immunoadjunctive therapy with nebulized rIFN-γ1b plus DOTS significantly reduced lung inflammatory cytokines in BAL supernatants at the 16 week time point. In order to investigate the mechanisms of these responses, nebulized rIFN-γ1b was used in eleven drug-sensitive tuberculosis patients, and found an increase in signaling molecules STAT-1, IRF-1 and IRF-9 (Condos, et al. (2003) Infect Immun 71: 2058-2064). In addition, nebulized rIFN-γ1b induced IP-10 downstream from these signaling molecules, but not inducible nitric oxide synthase (iNOS) (Nicholson, et al. (1996) J Exp Med 183: 2293-2302). There was a recruitment of lymphocytes and reduction in the neutrophil inflammation in the lung in all three groups, which manifested clinically as a dramatic resolution of the macrophage-neutrophilic alveolitis in the lower respiratory tract. Concomitantly with the increase in BAL lymphocytes, blood CD4+ cells doubled in their proliferative capacity to PPD or Mtb culture filtrate protein stimulation (data not shown) at the 4 week time point in both immunoadjunctive rIFN-γ1b groups of drug-sensitive pulmonary tuberculosis.

Immunoadjunctive therapy cleared *M tuberculosis* from the sputum and resolved the classic symptoms of fever, night sweats, wheeze, cough and malaise more rapidly than treatment with either DOTS or DOTS plus subcutaneous rIFN-γ1b. This finding demonstrates that nebulized rIFN-γ1b could reduce transmission due to more rapid clearance of *M tuberculosis* during the first 4 weeks. The subcutaneous rIFN-γ1b plus DOTS was not different from control since only nebulized rIFN-γ reaches the lower respiratory tract in pharmacological amounts to have a biological effect. All treatment groups experienced radiographic improvement with resolution of cavities by 16 weeks.

At 12 months there was only one study subject who had a treatment failure with culture positive sputum, and this occurred in the DOTS only control arm. TB Trials Consortium Study 22 comparing rifapentene and isoniazid once a week versus rifampicin and isoniazid twice a week reported bilateral pulmonary involvement and cavitation on chest radiograph were two risk factors (out of five) for treatment failure/relapse that occurred in 74/1004 (14.9%) of the TB patients (Tuberculosis Trials Consortium (2002) *Lancet* 360: 528-534). Although the numbers were much smaller, there were no treatment failures/relapses among the adjunctive rIFN-γ1b groups.

This is the first major report on the efficacy of rIFN-γ1b in a randomized clinical trial. In the first study of nebulized versus subcutaneous rIFN-γ in humans, IP-10 mRNA was detected in BAL cells only in the nebulized patients and not subcutaneous rIFN-γ treated subjects (Jaffe, et al. (1991) *J Clin Invest* 88: 297-302). This probably explains the finding that only nebulized rIFN-γ1b and not subcutaneous rIFN-γ1b was successful in clearing the sputum of Mtb and reducing the spontaneous release of inflammatory cytokines in 24 hour BAL supernatants. A pilot study of intramuscular rIFN-γ plus second-line anti-TB drugs over a 6-month period in 8 MDR-TB patients from Cuba showed sputum conversion over 1-3 months and marked improvement of radiographic abnormalities (Suárez-Méndez, et al. (2004) *BMC Infect Dis* 4: 44). Giosuè and colleagues nebulized IFN-α, a type I interferon, for 2 months as an adjunct in a randomized controlled clinical trial in 20 drug sensitive tuberculosis patients (Giosuè, et al. (1998) *Am J Respir Crit Care Med* 158: 1156-1162). Improvements in Mtb number in the sputum at 7 days, reduced fever by 7 days, reduced number of nodules and area of consolidation on CT-scans at 2 months, and significant decreases in BAL fluid amounts at 2 months of IL-1β, IL-6, and TNF-α were noted in the IFN-α group Giosuè, et al. (1998) *Am J Respir Crit Care Med* 158: 1156-1162). In a clinical trial of interleukin-2 adjunctive therapy performed in Uganda, 110 TB patients were randomized to IL-2 subcutaneously twice/day for the first 30 days in addition to DOTS versus DOTS alone. Seventeen percent versus 30% sputum conversion, respectively, was observed at 4 weeks (Johnson, et al. (2003) *Am J Respir Crit Care Med* 168: 185-191). Tramontana and colleagues conducted a clinical trial of thalidomide in TB patients blocking TNF-α leading to enhanced weight gain and increased serum IFN-γ in vivo (Tramontana, et al. (1995) *Mol Med* 1: 384-397).

Microarray analyses of BAL cells from TB patients shows elevated cytokine adhesion molecule ICAM, TGF-β, apoptosis genes, and IFN-γ pathway genes (Grassi, et al. (2006) *Clin Immunol* 121: 100-107). Immunohistochemistry of Mtb-laden lungs show increased IFN-γ, IL-12, IP-10, and TGF-β in granulomas and areas with pneumonitis with reductions in IL-10 and IL-4 compared to controls (Bai, et al. (2004) *Tuberculosis* 84: 375-385). BAL in Brazilian TB patients shows increased mRNA for TGF-βRI and II and IL-10 with increased protein for IFN-γ, IL-10, and bioactive TGF-β suggesting that TB has both stimulatory and counter-regulatory molecules that may ultimately down-regulate the Th1 response (Bonecini-Almeida, et al. (2004) *Infect Immun* 72: 2628-2634). Th2 cytokines may be inhibited by antagonists such as IL-4δ2 that may be increased in TB (Dheda, et al. (2007) *Tuberculosis* 87: 237-241). PBMC responses from TB patients to Mtb in vitro are reduced, probably due to L-10 which was increased in BAL cell supernatants. Gold and colleagues have reported low levels of Surfactant Protein A in BAL from involved segments of active TB along with increased IL-6, and reduced inhibitory C/EBPβ (Gold, et al. (2004) *Infect Immun* 72: 645-650).

BAL lymphocytes increased in all three groups after 4 months of therapy. Mtb is suppressive of the T cell immune response, e.g. IFN-γ response to PPD-stimulated PBMC is depressed and TGF-β and IL-10 are increased at the beginning of TB treatment and return to normal levels only at the end of treatment 6-9 months later (MacMicking, et al. (2003) *Science* 02: 654-659; Lienhardt, et al. (2002) *Eur J Immunol* 32: 1605-1613). In Gambian TB patients, T cell response to PPD from blood or pleural fluid was impaired pre-treatment, that changed to IFN-γ release after successful treatment or IL-4 after treatment failure; addition of IFN-α or IL-12 in vitro pre-treatment could alter the response to Th1 suggesting that immunotherapy could increase host defense against mycobacteria (Marchant, et al. (2001) *Am J Respir Cell Mol Biol* 24: 187-194). Significantly increased PBMC proliferative capacity to PPD occurred in the nebulized and subcutaneous rIFN-γ1b groups within 3-5 weeks of immunoadjunctive therapy.

Inflammatory cytokines IL-1β, IL-6, IL-8, IFN-γ and TNF-α as well as anti-inflammatory cytokines IL-10 and TGF-β (and its TGF-βRI and RII) are elevated in BAL from active TB patients (Toossi (2000) *Archivum Immunologiae et Therapiae Experimentalis* 48: 513-519). The inflammatory response in the lung in TB may include an increase in neutrophils, particularly in radiographically abnormal areas. Zhang and colleagues have previously reported that Mtb and its cell wall components stimulated IL-8 protein release and mRNA expression in vitro from alveolar macrophages (Zhang, et al. (1995) *J Clin Invest* 95: 586-592). In summary, the addition of nebulized recombinant interferon-γ1b to DOTS in a randomized, controlled clinical trial resulted in reduced BAL cytokines, more rapid clearance of Mth from the sputum, improved symptoms, and reduced inflammatory macrophage-neutrophil alveolitis. These findings demonstrate that nebulized recombinant interferon-γ1b may have a role in adjunctive immune stimulation in patients with cavitary tuberculosis.

Mechanisms of Action of Interferon-γ

Signal transduction pathways have been recently studied in cultured cells delineating a temporal regulatory pathway for the response to IFN-γ (Vilcek et al., (1994) *Int Arch Allergy Immunol* 104(4): 311-6; Young et al., (1995) *J Leukoc Biol* 58(4): 373-81). The first events take place when added IFN-γ binds to the extracellular domain of its receptor, and leads to tyrosine phosphorylation of preexisting signal transducer and activator of transcription 1 (STAT-1) at the intracellular domain of the receptor. Only tyrosine-phosphorylated STAT-1 is activated, which allows it to form homodimers (or heterodimers) and bind to a specific DNA sequence.

Upon translocating to the nucleus and binding to its cognate regulatory element in the promoters of many genes, STAT-1 activates transcription. STAT-1 can work with other preexisting transcription factors that are constitutively active, and thus transcription of some genes is maximally induced without a need for new protein synthesis. Other genes are regulated by STAT-1 together with transcription factors that are newly synthesized in response to IFN-γ. The IRF-1 gene, which also encodes a transcription factor, is also regulated by STAT-1 in response to IFN-γ (Pine, (1992) *J Virol* 66(7): 4470-8; Pine et al., (1994) *Embo J* 13(1): 158-67; Pine et al., (1990) *Mol Cell Biol* 10(6): 2448-57). It should be noted that the promoter of the IRF-1 gene also contains binding sites for nuclear factor kappa B (NF-kB), which mediates tumor necrosis factor alpha (TNF-α)-activated transcription of the IRF-1 gene (Harada et al., (1994) *Mol Cell Biol* 14(2):1500-9; R. Pine, unpublished).

Once the IRF-1 protein has been synthesized, it activates transcription of a temporally downstream set of genes. IRF-1 has been shown to regulate the IFN-γ-induced expression of key genes involved in antigen processing and presentation, including TAP-1, LMP-2, and HLA-A and HLA-B class I major histocompatibility antigens (Johnson et al., (1994) *Mol Cell Biol* 14(2): 1322-32; White et al., (1996) *Immunity* 5(4): 365-76).

IRF-1 is phosphorylated, and manipulating the extent of phosphorylation affects its DNA-binding activity (Pine et al., (1990) *Mol Cell Biol* 10(6): 2448-57; Nunokawa et al., (1994) *Biochem Biophys Res Commun* 200(2): 802-7). However, there is no clear evidence that phosphorylation of IRF-1 is regulated in vivo. STAT-1 activity is dependent on tyrosine phosphorylation and is affected by the extent of serine phosphorylation. However, the abundance of latent STAT-1 is also regulated. Cells treated overnight with IFN-γ have increased levels of STAT-1 protein, though the tyrosine phosphorylation and DNA-binding activity are only slightly greater than in unstimulated cells (Pine et al., (1994) *Embo J* 13(1): 158-67).

The study of gene expression and its regulation can provide information on other aspects of the overall immunological state. Specifically, functional effects of cytokine changes can be confirmed by determination of specific DNA-binding activities. For example, in T cells IL-12 leads to activation of STAT-4, while IL-4 leads to activation of STAT-6, the occurrence of Th1 and Th2 responses or a shift from one to the other may be reflected in the profile of STAT DNA-binding activities detected at a particular time (Darnell (1996) *Recent Prog Horm Res* 51:391-403; Ivashkiv, L. B. (1995) *Immunity* 3(1): 1-4).

Aerosolized Interferon-γ Treatment

Recently, a small randomized trial of patients with IPF were treated with subcutaneous interferon-γ (IFN-γ) (Ziesche et al. (1999) *N. Engl. J. Med.* 341:1264-1269). Analysis of transbronchial biopsy specimens obtained prior to and six months into therapy with IFN-γ, demonstrated that abnormal pretreatment increases in the profibrotic cytokines transforming growth factor-β (TGF-β) and connective-tissue growth factor (CTGF) were significantly reduced after treatment with IFN-γ (Ziesche et al. (1999) supra). Patients treated with prednisolone alone had no change in levels of TGF-β and CTGF.

Delivery of Interferons

Aerosol Delivery

In a broad aspect of the invention, a method of treating pulmonary diseases including tuberculosis, asthma and idiopathic pulmonary fibrosis (IPF) in a subject suffering from the pulmonary disease, comprising administering an aerosolized interferon such as interferon-γ in a therapeutically effective amount wherein the symptoms of the pulmonary disease are improved or ameliorated. In a preferred embodiment, aerosolized IFN-γ may be used for treating subjects suffering from tuberculosis wherein the subjects are insufficiently responsive to treatment with one or more antibiotics such as isoniazid and rifampicin.

Interferons such as IFN-γ may be administered by several different routes, including intravenous, intramuscular, subcutaneous, intranasally and via aerosol. However, when treating a pulmonary process alone, delivery of medication directly to the lung avoids exposure to other organ systems. Effective administration of 500 μg IFN-γ via aerosol three times per week for two weeks has been shown by bronchoalveolar lavage (BAL) analysis in normal patients to result in increased levels of IFN-γ post-administration. Likewise, about 500 micrograms of interferon-β three times per week and about 0.25 mg of interferon-α three times per week is thought to be effective.

It is an object of the present invention to deliver the interferon such as interferon-γ via the pulmonary route of administration. Interferons like IFN-γ are delivered to the lungs of a mammal while inhaling and traverses across the lung epithelial lining to the blood stream. (Other reports of this include Adjei et al., PHARMACEUTICAL RESEARCH, VOL. 7, No. 6, pp. 565-569 (1990); Adjei et al., *International Journal of Pharmaceutics,* 63:135-144 (1990); Braquet et al., *Journal of Cardiovascular Pharmacology*, Vol. 13, suppl. 5, s. 143-146 (1989); Hubbard et al., *Annals of Internal Medicine*, Vol. III, No. 3, pp. 206-212 (1989); Smith et al., *J. Clin. Invest*., Vol. 84, pp. 1145-1146 (1989); Oswein et al., "*Aerosolization of Proteins*", Proceedings of Symposium on Respiratory Drug Delivery H, Keystone, Colo., March, 1990; and Platz et al., U.S. Pat. No. 5,284,656. Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this invention are the ULTRAVENT® nebulizer, manufactured by Mallinckrodt, Inc., St. Louis, Mo.; the ACORN II® nebulizer, manufactured by Marquest Medical Products, Englewood, Colo.; the VENTOLIN® metered dose inhaler, manufactured by Glaxo Inc., Research Triangle Park, N.C.; and the SPINHALER® powder inhaler, manufactured by Fisons Corp., Bedford, Mass., MISTYNEB®, manufactured by Allegiance, McGraw Park, Ill.; AEROECLIPSE®, manufactured by Trudell Medical International, Canada.

All such devices require the use of formulations suitable for the dispensing of protein. Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified protein may also be prepared in different formulations depending on the type of chemical modification or the type of device employed.

Formulations suitable for use with a nebulizer, either jet or ultrasonic, may typically comprise protein dissolved in water at a concentration of about 0.1 to 25 mg of biologically active protein per mL of solution. The formulation may also include a buffer and a simple sugar (e.g., for protein stabilization and regulation of osmotic pressure). The nebulizer formulation may also contain a surfactant, to reduce or prevent surface induced aggregation of the protein caused by atomization of the solution in forming the aerosol.

Formulations for use with a metered-dose inhaler device may generally comprise a finely divided powder containing the protein suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device may comprise a finely divided dry powder containing protein and may also include a bulking agent, such as lactose, sorbitol, sucrose, or mannitol in amounts which facilitate dispersal of the powder from the device, e.g., 50 to 90% by weight of the formulation. The protein should most advantageously be prepared in particulate form with an average particle size of less than 10 μm (or microns), most preferably 0.5 to 5 μm, for most effective delivery to the distal lung.

It is a goal of aerosol delivery to significantly increase the delivery of therapeutic agents such as interferons, including IFN-γ, to the deep lung in humans. A particularly preferred approach to breathing slow and deep inspiration may, when compared with standard (tidal breathing), increase deposition efficiency in the lung periphery by a factor of up to about 50 times.

Figure 2:
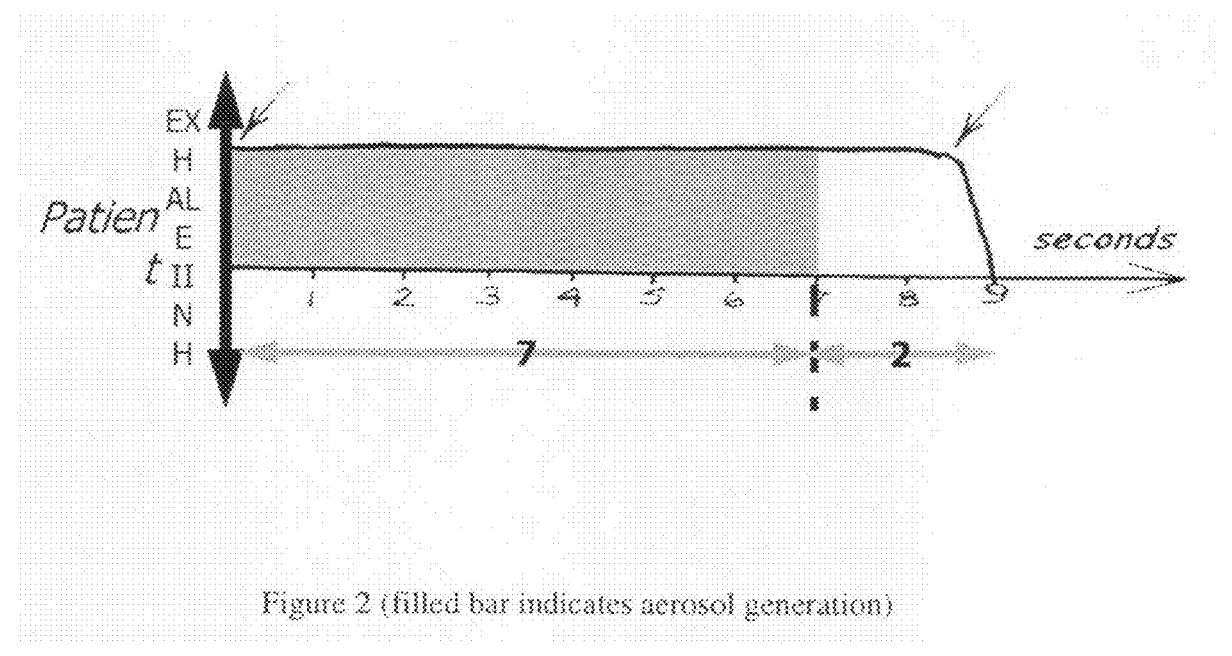

The specific pattern of breathing using a method of slow and deep inspiration as compared to tidal breathing (FIG. 1) describes a reduction in inspiratory flow and a greatly prolonged inspiratory time. This pattern is shown in FIG. 2. The slow inspiration allows aerosol particles to bypass the upper airways thus making them available for deposition in the lung. The prolonged inspiration allows for suitable settling of aerosols in the lung periphery. The prolongation of the inspiratory time and the advanced settling promotes "inspiratory deposition" before remaining particles can be exhaled. It is possible under these circumstances to have almost 100% of the inhaled particles depositing before exhalation begins. This process can be further enhanced by using particles that are relatively large (e.g., about 4.5 μm) that ordinarily would deposit in the oropharynx. The prolonged inspiration of slow and deep breathing is particularly suited for delivery of drugs to the lungs of patients whose peripheral airway pathology results in reduced deposition of conventional smaller aerosols as well as promoting avoidance of deposition in the oropharynx. Diseases of the lung periphery that may be treated by this method include, for example, idiopathic pulmonary fibrosis and emphysema. Both these entities result in enlarged airspaces that result in minimal deposition during tidal breathing.

Figure 3:
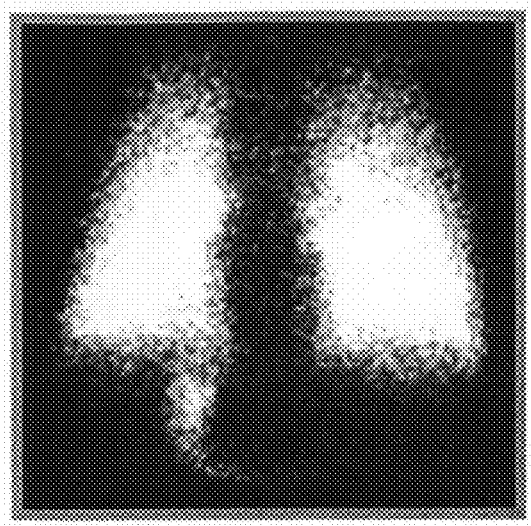
FIG. 3 represents a deposition pattern in a human subject inhaling 4.5 μm aerosols using the slow and deep breathing pattern. The images demonstrate minimal deposition of aerosol (less than 10%) in the upper airways illustrated by the small amount of activity in the stomach. The deposition image represents radiolabeled aerosol deposited in the lung periphery of a human subject after 3 breaths using the slow and deep pattern with an inspiratory time of approximately 8 seconds.
Figure 4:
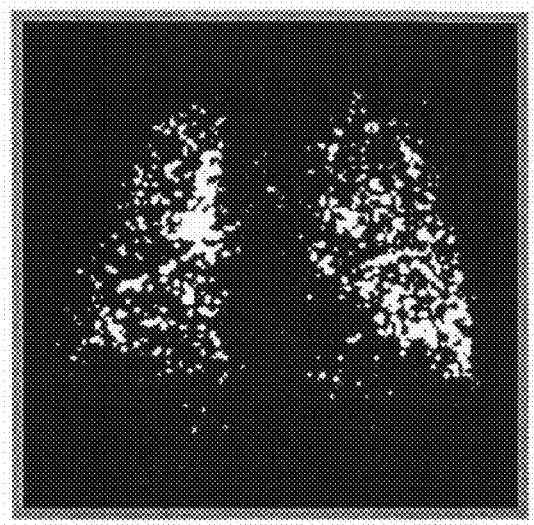
FIG. 4 is an illustrative scan in the same subject following 20 breaths of tidal breathing of 1.5 μm particles which is the present standard mode of inhalation. Analysis of the images indicates that the slow and deep method of breathing which incorporates the use of large particles, slow inspiration and a prolonged inspiratory time is 51 times more efficient per breath in depositing aerosol particles in the lung.
Figure 5:
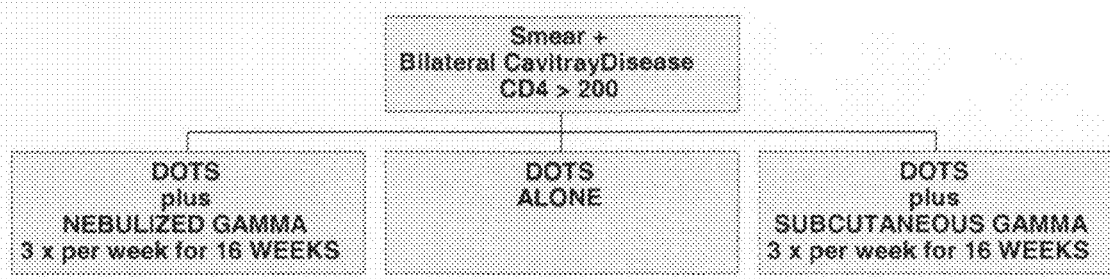
FIG. 5 represents the protocol followed to assess the efficacy of interferon-γ in tuberculosis patients. One group of evaluable patients were given standard therapy supplemented by nebulized interferon-γ (NEB), another group received standard therapy alone (DOTS), and a third group received standard therapy supplemented by subcutaneous interferon-γ (SUB).

This technique of inhalation and deposition can enhance the peripheral delivery of drug with the intent of promoting systemic absorption into the systemic circulation via the pulmonary capillaries. FIG. 3 represents a deposition pattern in a human subject inhaling 4.5 μm aerosols using the slow and deep breathing pattern. The images demonstrate minimal deposition of aerosol (less than 10%) in the upper airways illustrated by the small amount of activity in the stomach. The deposition image represents radiolabeled aerosol deposited in the lung periphery of a human subject after 3 breaths using the slow and deep pattern with an inspiratory time of approximately 8 seconds. FIG. 4 is an illustrative scan in the same subject following 20 breaths of tidal breathing of 1.5 μm particles which is the present standard mode of inhalation. Analysis of the images indicates that the slow and deep method of breathing which incorporates the use of large particles, slow inspiration and a prolonged inspiratory time is 51 times more efficient per breath in depositing aerosol particles in the lung.

The manufacture of devices capable of performing the slow and deep maneuver is complex, but prototype devices that perform this function are being developed and have been utilized (Profile Therapeutics, Inc. 28 State Street, Ste. 1100, Boston, Mass. 02109, which is a subsidiary of Profile Therapeutics which has its main offices in the UK).

Diseases of the lung parenchyma result in geometric changes in the lung periphery that can minimize the deposition of inhaled particles. Therapeutics delivered directly to the site of disease (the lung periphery) can be more effective when compared to the same agent delivered systemically. A method of slow and deep inhalation of an interferon, such as IFN-γ, aerosol is particularly suited to the treatment of disease in the alveoli of patients with obstructive disease such as pulmonary fibrosis.

Human deposition studies have indicated that a slow and deep inhalation method is about 50 times more efficient than conventional systems of aerosol delivery. This breathing pattern allows the design of clinical trials to test the efficacy of aerosol therapy for pulmonary diseases such as obstructive pulmonary diseases, including, for example, idiopathic pulmonary fibrosis or asthma with agents such as interferons, including, for instance, INF-γ, over a wide range of dosing to the lung periphery utilizing existing formulations of this agent. Quantities deposited in the lung are controlled by the pattern of breathing because virtually no aerosol is exhaled.

Nasal Delivery

Nasal delivery of the protein is also contemplated. Nasal delivery allows the passage of the protein to the blood stream directly after administering the therapeutic product to the nose, without the necessity for deposition of the product in the lung. Formulations for nasal delivery include those with dextran or cyclodextran.

Dosages

It is understood that as further studies are conducted, information will emerge regarding appropriate dosage levels for treatment of various conditions in various patients, and one of ordinary skill in the art, considering the therapeutic context, age and general health of the recipient, will be able to determine proper dosing. Generally, for injection or infusion, interferon-γ dosage will be between 100 μg of biologically active protein (calculating the mass of the protein alone, without chemical modification) to 750 μg (based on the same) given two to five, often three times per week. More preferably, the dosage may be about 200 to 300 μg given three times per week. Generally, for injection or infusion, interferon-α dosage is generally 100 to 750 micrograms administered one to five times per week, preferably about 500 micrograms administered three times per week. In the instance of interferon-β, dosage is generally 0.10 to 1 mg one to three times per week, preferably about 0.25 mg three times per week. The dosing schedule may vary, depending on the circulation half-life of the protein, and the formulation used.

Administration with Other Compounds

It is a further aspect of the present invention that one may administer the interferon in conjunction with one or more pharmaceutical compositions used for treating a pulmonary disease. Also, antibiotic, anti-inflammatory or immunosuppressive agents may be co-administered, eg. isoniazid, rifampin, cyclophosphamide, azathioprine or corticosteroids. Administration may be simultaneous or may be in serriatim.

It has been shown that after subcutaneous administration of 250 μg IFN-γ for three days, there was no increase in BAL levels of IFN-γ or alteration of alveolar macrophages, while there was upregulation of peripheral blood monocytes (Jaffe et al. (1991) *J. Clin. Invest.* 88:297-302).

In the studies described below, patients unresponsive to conventional immunosuppressive therapy suffering from IPF were treated with aerosolized IFN-γ.

The invention may be better understood by reference to the following examples, which are intended to be exemplary of the invention and not limiting thereof.

EXAMPLES

The following examples are put forth so as to provide those of ordinary skill in the art with a complete disclosure and description of how to make and use the therapeutic methods of the invention and compounds and pharmaceutical compositions, and are not intended to limit the scope of what the inventors regard as their invention. Efforts have been made to ensure accuracy with respect to numbers used (e.g., amounts, temperature, etc.), but some experimental errors and deviations should be accounted for. Unless indicated otherwise, parts are parts by weight, molecular weight is average molecular weight, temperature is in degrees Centigrade, and pressure is at or near atmospheric.

Example 1

Each patient was asked to participate in a deposition study (under separate consent) of IFN-γ administered via hand-held nebulizer. This deposition study was designed to study aerosolized IFN-γ as follows. The drug was labeled with 99 mTc and administered via aerosol nebulizer. Using the "attenuation technique", the dose of IFN-γ delivered to various regions of the lung was calculated. The initial dose of 500 μg IFN-γ was used, as this dose has previously been shown to be safe. The dose is adjusted according to deposition studies in each individual patient. A follow up bronchoscopy was performed at the end of the therapy, using the protocol described above. BAL was guided by lung deposition images, so that the areas of highest drug deposition was analyzed and compared to areas of lowest delivered drug and pre-aerosol IFN-γ samples. In this way, total dose to each area of the lung can be calculated and determined. Depending on clinical response and BAL data, dose may be adjusted to reflect optimal clinical and deposition parameters. Attempts will be made to sample similar segments pre- and post-treatment, when possible. Each patient has a follow up evaluation at one month post therapy. The results of all procedures, laboratory evaluations, radiological studies, and pulmonary physiology evaluations are documented in the patient's medical record. All study evaluations are conducted at the GCRC of NYU Medical Center.

One commercially available breath-actuated nebulizer was used in this study, the AEROECLIPSE®, whose particle generation is dependent on patient breathing through the nebulizer. It produces aerosol only during inspiration.

IFN-γ was radiolabeled using $^{99m}$Technetium diethylene triaminepenta-acetic acid ($^{99m}$Tc-DTPA) for both in vitro and in vivo studies. For AEROECLIPSE®, 2 vials (250 mg of IFN-γ) were used to make up a final volume of 2 mL AEROECLIPSE® was operated using a Pari Master air compressor (PARI Respiratory Equipment, Inc. Monterey, Calif.)

The nebulizers were connected to the circuit in the manner of their clinical use. A ten stage, low flow (1.0 L/m) cascade impactor (California measurements, Sierra Madre, Calif.) was connected using a T connector (T connector$_{cascade}$, Hudson Respiratory Care, Temecula, Calif.). An inspiratory filter, that prevented particles from entering the cascade impactor during expiration, was placed between the piston pump and cascade impactor. A second filter (leak filter) was placed in the system to capture the excess particles directed neither to the inspiratory filter nor to the impactor. To assess possible effects of patient ventilation a piston pump (Harvard Apparatus, Millis, Mass.) was used to simulate a patient's breathing effort.

B Prior to Inhalation the Aerosol was Studied on the Bench Under Two Conditions:

Standing cloud: The cascade impactor sampled the particles directly from the tubing at 1 Lpm without any ventilation generated by the piston pump (pump disconnected from circuit). For the purpose of generation of particles from AEROECLIPSE®, the breath actuation valve was pressed manually for the duration of sampling.

During Ventilation: The Harvard pump was used to generate a sinusoidal flow in the system, analogous to the breathing of a patient. A tidal volume of 750 mL; Respiratory Rate of 20/m and Duty Cycle of 0.5 was used.

Aerodynamic particle distributions were measured as well as deposition on the connecting tubing to the cascade (T connector$_{cascade}$). The ballistic properties of the aerosol were quantified as the activity on the T connector$_{cascade}$ and reported as a percentage of the activity captured in the cascade impactor (% Cascade). This deposition was used in predicting lung deposition.

Xenon imaging and attenuation studies For all the subjects IFN-γ deposition was studied using the AeroEclipse nebulizer. Xenon imaging and attenuation studies (see below) were performed.

Lung volume and outline studies ($^{133}$Xenon ($^{133}$Xe) equilibrium scan) The patient was seated in front of a posteriorly positioned gamma camera (Picker Dina camera; Northford, Conn.). After taking a room background image for $^{99m}$Technetium ($^{99m}$Tc), the camera was set for $^{133}$Xe. Breathing tidally at functional residual capacity (FRC), the patient inhaled 5-10 mCi of $^{133}$Xe until the count rate became stable ±10% over 15 seconds. A 1.0 min gamma camera image ($^{133}$Xe equilibrium image) was acquired and stored in a computer (Nuclear Mac v1.2/94; Scientific Imaging Inc. Littleton, Colo.) for analysis. This image was used to define the outer margins of the lung.

Aerosol deposition studies After $^{133}$Xe imaging, the camera was switched to $^{99m}$Tc. Then, the patient inhaled radiolabeled aerosolized IFN-γ from the nebulizer. For each device an expiratory filter was present to capture exhaled particles. The nebulizers were run until dry. After final inhalation, the patient drank a glass of water to wash material from the oropharynx to the stomach. Measuring stomach activity assessed upper airway deposition.

Lung attenuation studies (perfusion scan) Lung perfusion scanning was done to calculate the attenuation factor of the lungs. Immediately following deposition imaging, 5 mCi of $^{99m}$Tc-albumin macroaggregates were injected via a peripheral vein. It was assumed that all the macroaggregates traversed the right side of the heart and distributed in the lung proportionately to regional perfusion. A one-minute image was obtained. Perfusion was calculated as measured activity minus the activity measured on the previous (deposition) image. The lung attenuation factor was measured by dividing the amount of activity measured by the camera by the amount of activity injected. Lung attenuation factor=Activity measured/activity injected Stomach Attenuation The patient was given bread with a known amount of $^{99m}$Tc applied to it and a gamma camera picture of the stomach was taken after ingestion. Stomach attenuation was calculated by dividing the activity ingested by activity measured by the gamma camera. Stomach attenuation factor=Activity measured/activity ingested Quantification of deposition Using the computer, regions of interest were visually drawn around the stored equilibrium $^{133}$Xe equilibrium scan to define the lung outline and encompass the lung volume. Central lung regions were then drawn that outlined the inner one third of the two-dimensional lung area. After the xenon regions were defined, the same regions were placed over the deposition image and stomach activity identified. Then, a "stomach region" was visually drawn outlining the stomach. If there was overlap between the stomach region and the xenon equilibrium region of the left lung, the overlapping region was defined as "stomach on lung" or SOL. For determination of whole lung deposition, radioactivity from the stomach and the stomach on lung regions were excluded.

Lung deposition was measured using the gamma camera by quantifying activity in the lung regions and applying the appropriate attenuation correction. Oropharyngeal deposition was determined by subtracting the lung activity from the total activity on the deposition image. Appropriate corrections were made for stomach attenuation.

Specific Central to Peripheral ratio (sC/P) Specific central to peripheral lung activity was defined by dividing the aerosol image by the xenon equilibrium image. This ratio represents the distribution of deposited aerosol normalized for regional lung volume.

sC/P for aerosol deposition=(C/P aerosol/C/P xenon)

If the aerosol behaves perfectly as a gas and follows the $^{133}$Xe distribution, the sC/P ratio should be 1.0. Particles that deposit preferentially in central airways yield sC/P ratios of 2.0 or higher.

Results of Deposition study show significant deposition of aerosol throughout the lungs. When normalized for lung volume, there are relatively more particles in central lung regions than peripheral (sC/P ratio=1.618. There is minimal upper airway deposition.

Example 2

Effects of Aerosol IFN-γ

Adverse effects. We treated 15 individuals (normal volunteers and patients with pulmonary tuberculosis) with aerosolized IFN-γ. The aerosol administration was well tolerated with few patients complaining of occasional cough or myalgias. The longest period of administration was 3 months without an increase in adverse effects. In addition, Jaffe found that aerosolized IFN-γ given to normal subjects was safe, without systemic side effects, and was able to activate alveolar macrophages and not PBMC, as opposed to parenterally delivered r IFN-γ, the effects of which could only be noted in the peripheral blood (Jaffe et al., (1991) *J Clin Invest* 88(1): 297-302).

Deposition studies. We investigated the aerosol deposition characteristics of IFN-γ. A deposition image is shown and reveals that radioactivity (aerosol) is deposited to all normal areas of the lung. Disease and cavitary areas are spared. Perfusion scan shows minimal perfusion to cavitary areas as well. Preliminary determination of deposition reveals a range of 10-20% of aerosol dose delivered to the lung, using both mass-balance technique and xenon (figure). We concluded that targeted delivery of drug to the lung results in drug deposition in normal lung parenchyma (Condos et al., (1998) *Am J Respir Crit Care Med* 157(3): A187).

Bronchoalveolar lavage findings. We previously demonstrated clinical improvement in a group of patients with severe multi-drug resistant tuberculosis treated with IFN-γ. The patients underwent bronchoscopy with BAL of the radiographically involved area before and after treatment. 24-hour cell culture supernatants and fluid from the BAL were assayed by ELISA and were found to have decreasing levels over time of TNF-a (mean 172 to 117 pg/ml), IL 1-b (mean 25 to 8 pg/ml) and no appreciable levels of IFN-γ (mean 3.3 to 2.5 pg/ml). We concluded that IFN-γ administration is associated with a decrease in TNF-a produced locally at sites of disease. This may in part explain the beneficial effects of IFN-γ in advanced in advanced MDR-TB (Condos et al., (1998) *Am J Respir Crit Care Med* 157(3): A187).

Example 3

Cytokine Gene Regulation

In this study investigation of transcription factor abundance, phosphorylation, and DNA binding activities test the hypothesis that aerosol IFN-γ treatments impinge on cellular signal transduction pathways to activate latent STAT-1 and induce de novo synthesis of IRF-1. We performed these experiments on BAL cells obtained from uninvolved and involved areas of lung in patients with pulmonary tuberculosis pre and post treatment with IFN-γ (Condos et al., (1999) *Am J Respir Crit Care Med* (in press)). Purifying and cloning IRF-1 was a principal part of the initial work performed by Richard Pine, Ph.D., in the Laboratory of Molecular Cell Biology at Rockefeller University with James E. Darnell, Jr. (Pine et al., (1990) *Mol Cell Biol* 10(6): 2448-57). Immunoblot and electrophoretic mobility shift assays the same as or similar to those proposed for Aim 3 of this project have been employed in the work mentioned here.

The results of cytokine gene manipulation in the uninvolved lungs of tuberculosis patients is most relevant. Results show that in both the adherent (mainly alveolar macrophages) and the nonadherent (lymphocytes and polymorphonuclear cells) portions of the BAL cells, there is an increase in the amount of specific IRF-DNA and STAT-1-DNA complexes after aerosol IFN-γ treatment.

Example 4

A randomized clinical trial was performed to look at interferon-gamma immunomodulation in tuberculosis (TB) patients. Sputum smear-positive tuberculosis patients with bilateral cavitary disease on chest radiographs were randomized to receive standard tuberculosis directly observed therapy (DOTS) or DOTS therapy supplemented with interferon gamma three times per week for 16 weeks. Endpoints of the study included relapse rates, symptoms, culture conversion and radiographic resolution of cavitary disease and scarring. Immunnomodulation was investigated by using molecular biology techniques to assess changes in both bronchoalveolar lavage and peripheral blood of treated patients before and after interferon gamma treatment. Interferon-gamma was given either by subcutaneous injection or as an aerosol via nebulizer. 100 patients were randomized. Review of data, in an intention to treat analysis, reveals a significant decrease in fever, sputum volume and wheeze in the gamma treated group. This improvement was earlier and more sustained in the aerosol treated group. In addition, aerosol gamma led to earlier sputum culture conversion at 30 days when compared to standard therapy alone (DOTS) or standard therapy plus interferon gamma by subcutaneous injection.

We conducted the randomized control trial at two recruitment sites, one in New York and one in Cape Town, South Africa. 100 patients were enrolled. Sputum smear-positive tuberculosis patients with bilateral cavitary disease on chest radiographs were randomized to receive standard tuberculosis directly observed therapy (DOTS) or DOTS therapy supplemented with interferon gamma three times per week for 16 weeks. For patients randomized to either of the two treatment arms, recombinant interferon gamma (ACTIMMUNE®, InterMune, Inc, Brisbane, Calif.) was delivered 3 times weekly either via the high efficiency AEROECLIPSE® nebuliser (Trudell Medical International, Canada) at a dose of 200 mcg or via subcutaneous injection at the equivalent 200 mcg dose strength. Immunotherapy dosing continued for a 16 week period with strict DOTS adherence monitoring.

Of the 100 patients randomized, 20 were excluded for various reasons including negative cultures, withdrawal of consent, lost to follow up, death or concomitant illness such as hepatitis. 80 patients were evaluated clinically. Of the 80 patients evaluated, 29 received nebulized interferon γ supplied by Intermune, Brisbane, Calif. and administered with an AERO ECLIPSE® nebulizer, manufactured by Trudell Medical International, Canada. 28 patients received standard therapy (DOTS), and 23 received subcutaneous interferon γ supplied by Intermune, Brisbane, Calif. Endpoints of the study included relapse rates, symptoms, culture conversion and radiographic resolution of cavitary disease and scarring. Immunnomodulation was investigated by using molecular biology techniques to assess changes in both bronchoalveolar lavage and peripheral blood of treated patients before and after interferon gamma treatment.

Patients were asked at weekly intervals whether they had experienced fever in the past week, whether they had experienced a reduction in sputum production over baseline, and whether they had experienced a reduction in wheezing over baseline. Further, cultures were taken of the sputum to determine whether the cultures were still positive for tuberculosis pathogens. Review of data, in an intention to treat analysis, reveals a significant decrease in fever, sputum volume and wheeze in the treated group. This improvement was earlier and more sustained in the aerosol treated group. In addition, aerosol gamma led to earlier sputum culture conversion at 30 days when compared to standard therapy alone (DOTS) or standard therapy plus interferon gamma by subcutaneous injection.

Figure 6:
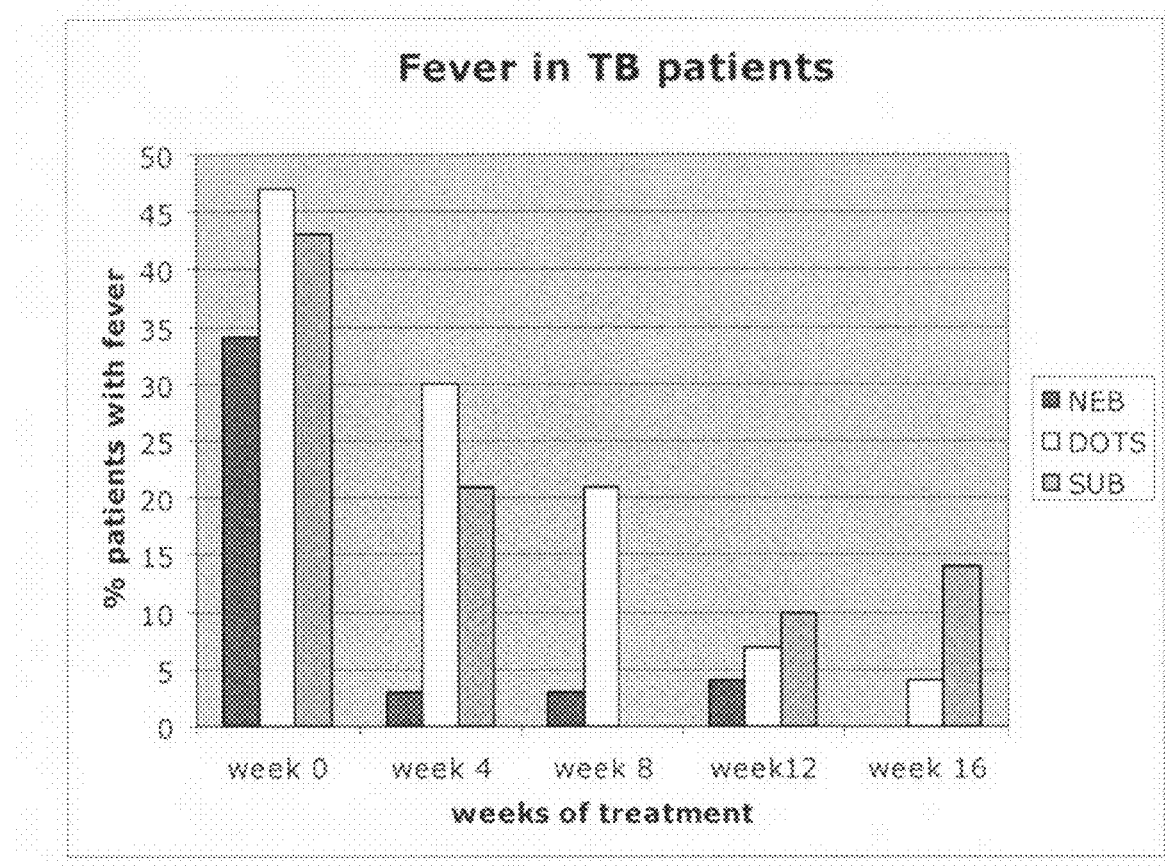
FIG. 6 represents graphically that over a sixteen week period of time, there was a reduction in reported fever among patients in all of the three treatment groups described in FIG. 5. However, the difference was most pronounced in the group treated with standard therapy supplemented by nebulized interferon-γ. p<0.05 at weeks 4 and 8.
Figure 7:
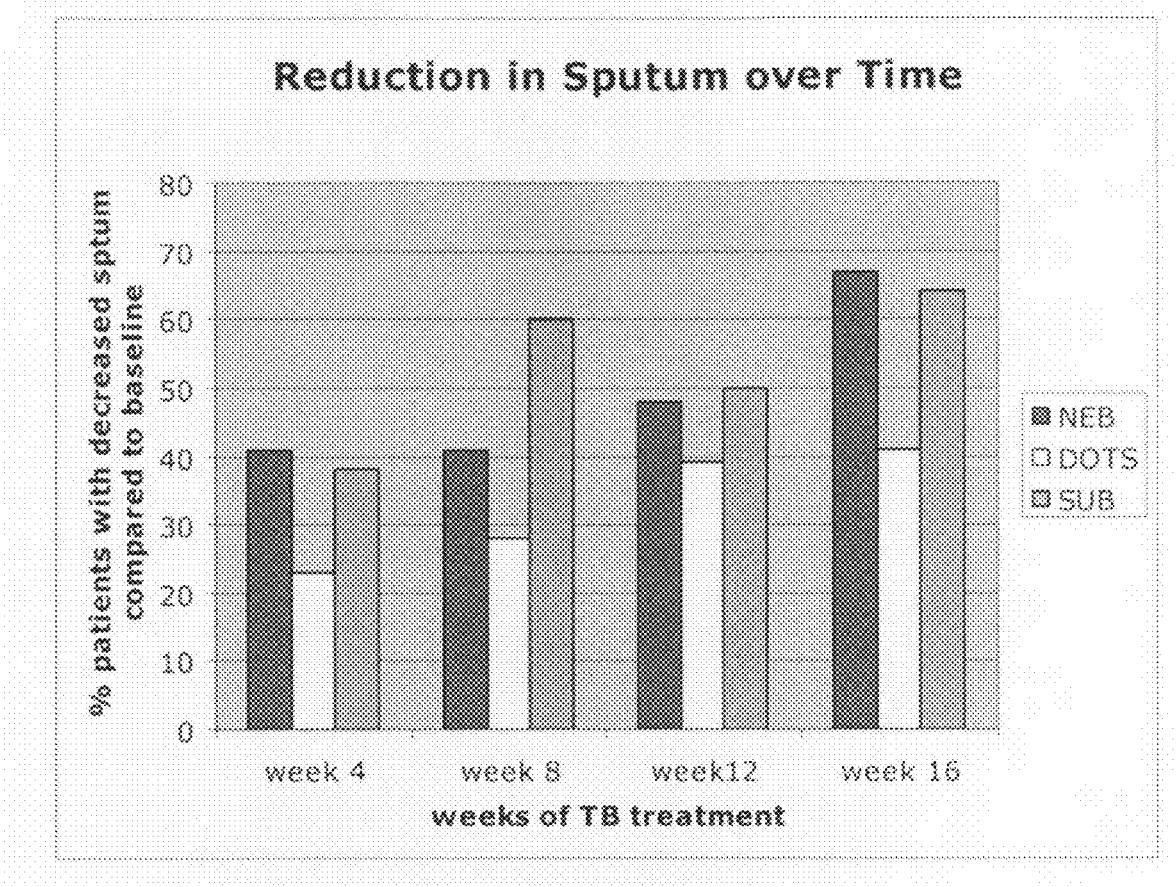
FIG. 7 represents graphically that over a sixteen week period of time, there was a reduction in sputum production among patients in all of the three treatment groups described in FIG. 5. However, the difference was most pronounced in the group treated with standard therapy supplemented by nebulized interferon-γ. p<0.05 at week 8 compared to standard therapy (DOTS) alone and p<0.05 at week 16 with combined interferon-γ therapy compared to standard therapy (DOTS) alone.
Figure 8:
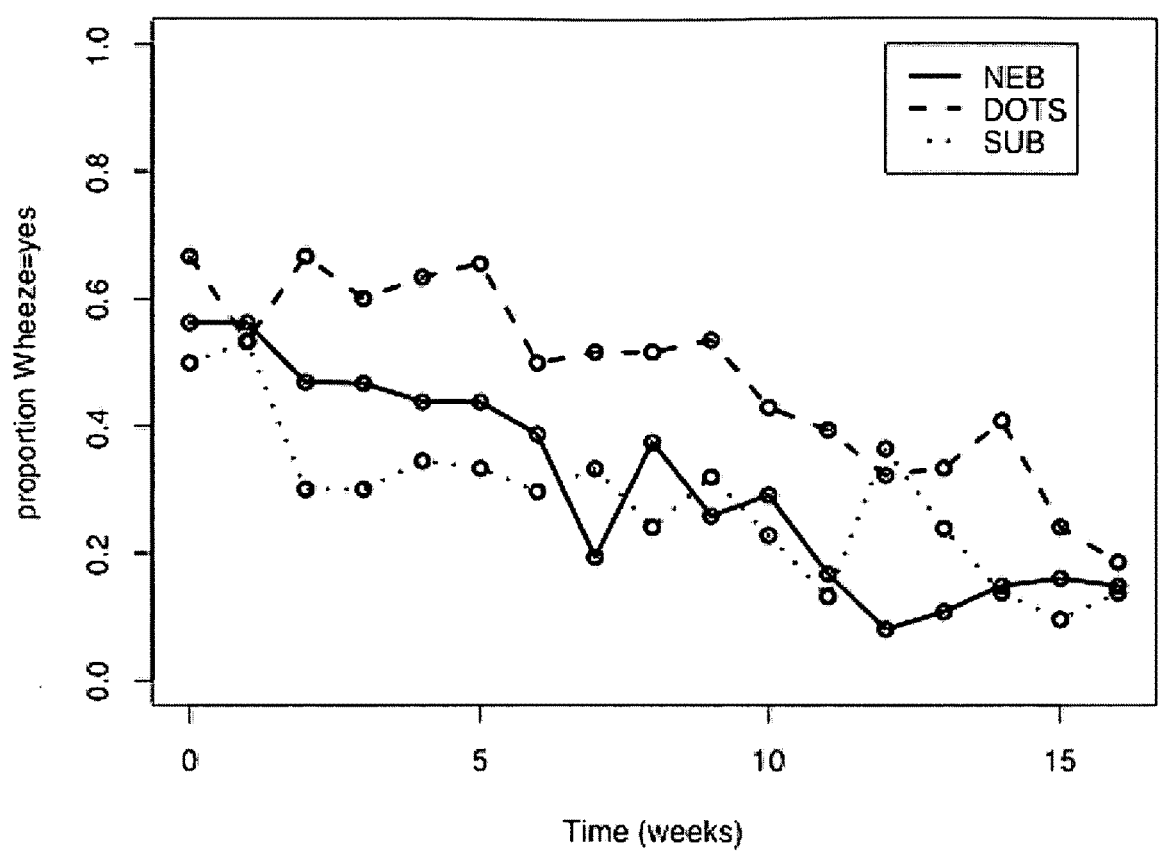
FIG. 8 demonstrates graphically that over a sixteen week period of time, there was a reduction in wheezing among patients in all of the three treatment groups described in FIG. 5. However, the difference more pronounced in the group treated with standard therapy supplemented by nebulized interferon-γ than in the group treated with standard therapy alone.
Figure 9:
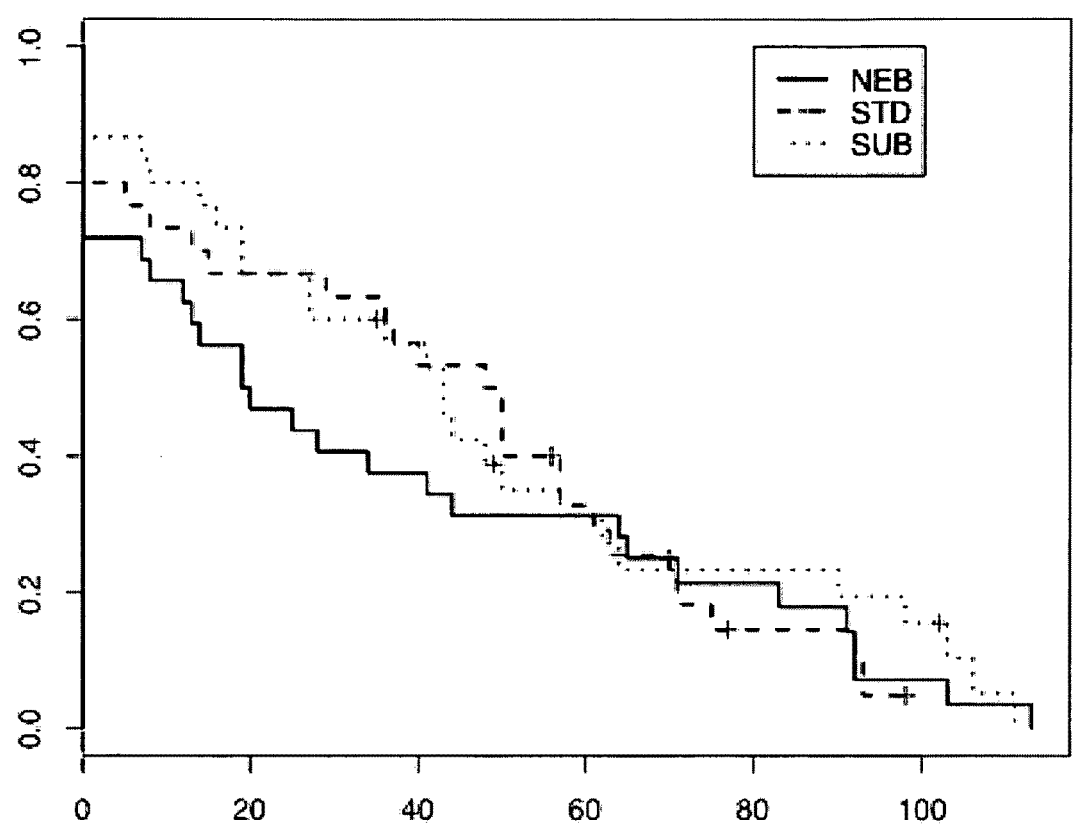
FIG. 9 demonstrates graphically that over a sixteen week period of time, there was increased conversion of sputum cultures to negative for tuberculosis pathogens in all of the three treatment groups described in FIG. 5. However, the difference was more pronounced in the group treated with standard therapy supplemented by nebulized interferon-γ than in the group treated with standard therapy alone.

FIG. 6 represents graphically that over a sixteen week period of time, there was a reduction in fever among patients in all of the three treatment groups. However, the difference was most pronounced in the group treated with standard therapy supplemented by nebulized interferon-γ. FIG. 7 demonstrates graphically that over a sixteen week period of time, there was a reduction in sputum production among patients in all of the three treatment groups. However, the difference more pronounced in the group treated with standard therapy supplemented by nebulized interferon-γ than in the group treated with standard therapy alone. FIG. 8 demonstrates graphically that over a sixteen week period of time, there was a reduction in wheezing in all of the three treatment groups. However, the difference was more pronounced in the group treated with standard therapy supplemented by nebulized interferon-γ than in the group treated with standard therapy alone. FIG. 9 demonstrates graphically that over a sixteen week period of time, there was an increase in conversion of sputum cultures to negative for tuberculosis pathogens in all of the three treatment groups. However, the difference was more pronounced in the group treated with standard therapy supplemented by nebulized interferon-γ than in the group treated with standard therapy alone.

Figure 10:
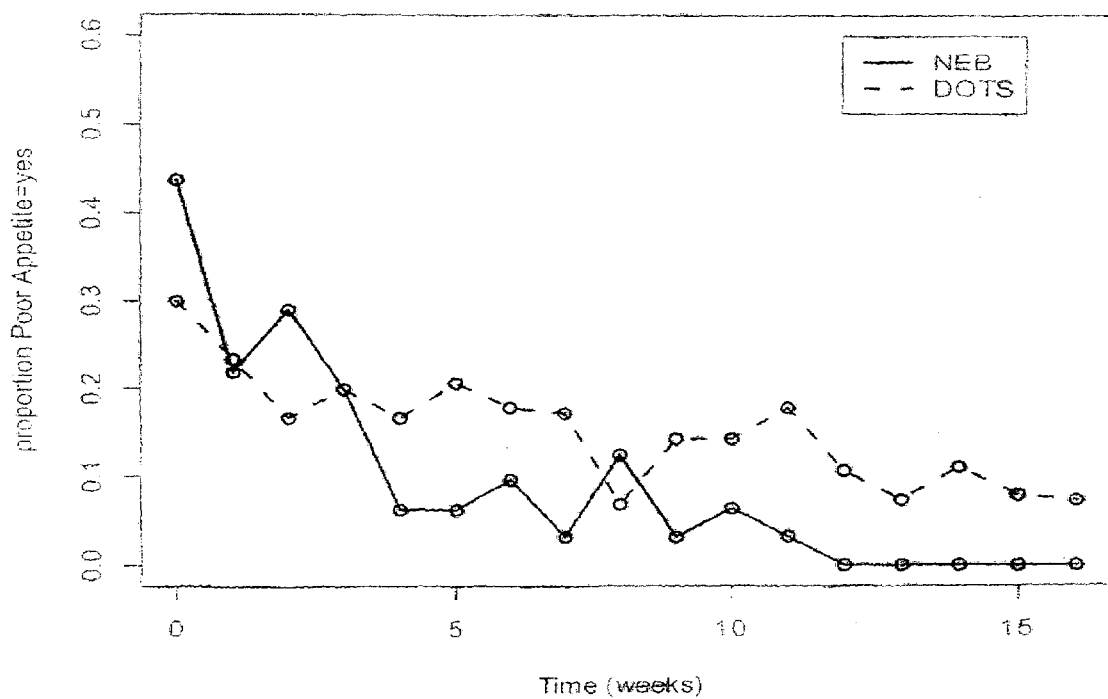
FIG. 10 represents graphically that over a sixteen week period of time, there was a reduction in reported patients having a poor appetite in patients receiving nebulized interferon-γ therapy and standard therapy. However, the reduction in poor appetite was most pronounced in the group treated with standard therapy supplemented by nebulized interferon-γ.
Figure 11:
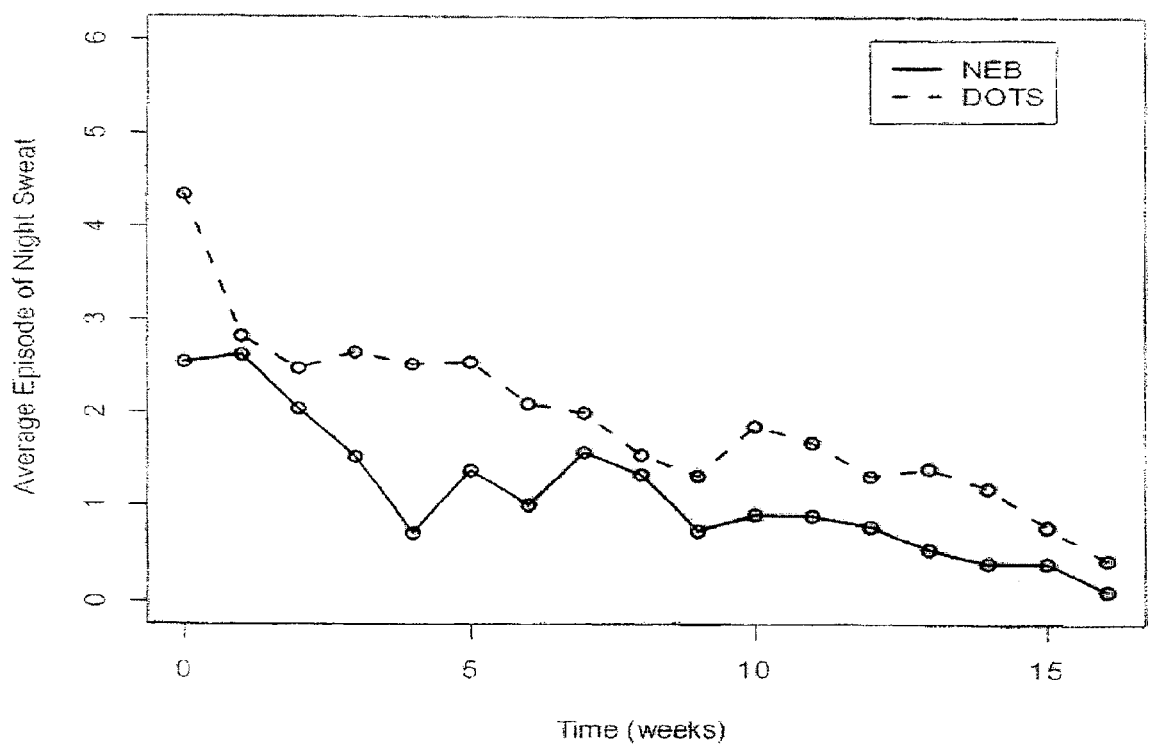
FIG. 11 represents graphically that over a sixteen week period of time, there was a reduction in reported patients experiencing night sweats in patients receiving nebulized interferon-γ therapy and standard therapy. However, the reduction in night sweats was most pronounced in the group treated with standard therapy supplemented by nebulized interferon-γ.
Figure 12:
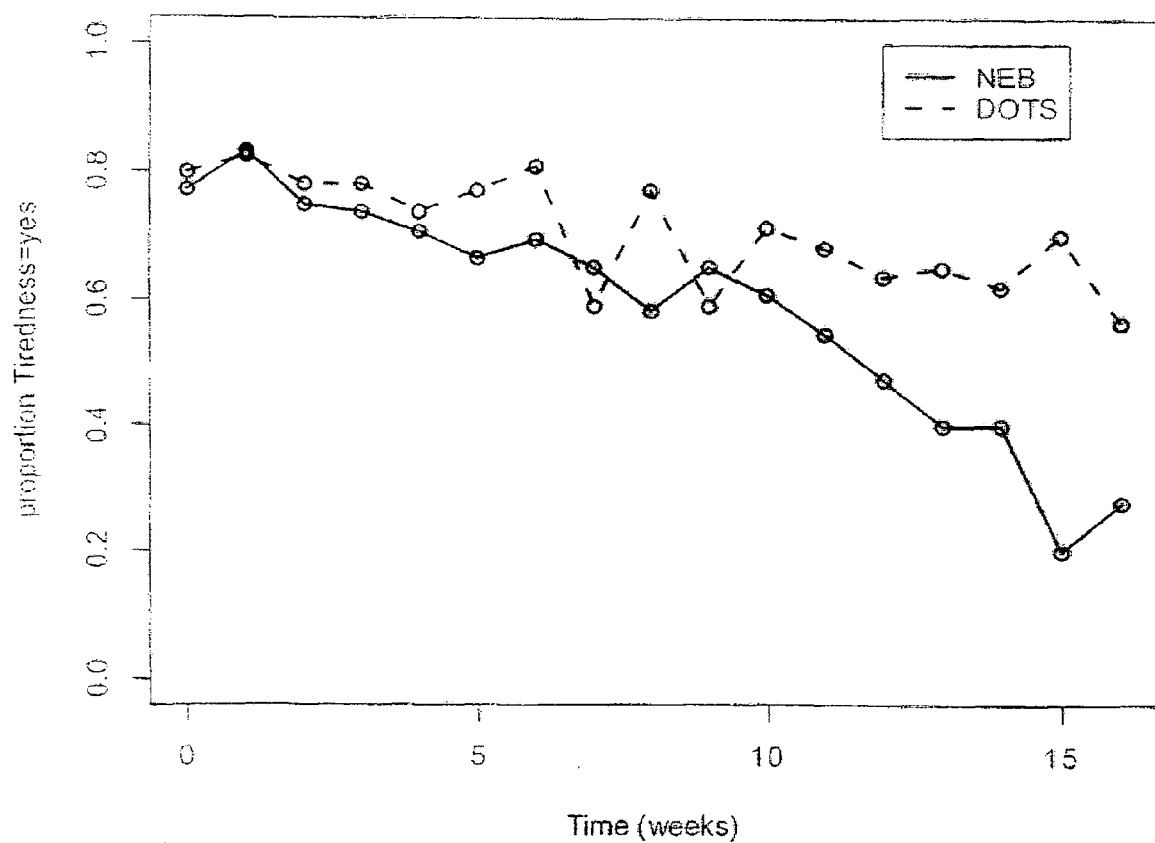
FIG. 12 represents graphically that over a sixteen week period of time, there was a reduction in patients reporting tiredness both in patients receiving nebulized interferon-γ therapy and standard therapy. However, the reduction in tiredness was most pronounced in the group treated with standard therapy supplemented by nebulized interferon-γ.

FIG. 10 represents graphically that over a sixteen week period of time, there was a reduction in reported patients having a poor appetite in patients receiving nebulized interferon-γ therapy and standard therapy. However, the reduction in poor appetite was most pronounced in the group treated with standard therapy supplemented by nebulized interferon-γ. Likewise, FIG. 11 represents graphically that over a sixteen week period of time, there was a reduction in reported patients experiencing night sweats in patients receiving nebulized interferon-γ therapy and standard therapy. However, the reduction in night sweats was most pronounced in the group treated with standard therapy supplemented by nebulized interferon-γ. Further, FIG. 12 represents graphically that over a sixteen week period of time, there was a reduction in patients reporting tiredness both in patients receiving nebulized interferon-γ therapy and standard therapy. However, the reduction in tiredness was most pronounced in the group treated with standard therapy supplemented by nebulized interferon-γ.

Example 5

Materials and Methods. Patients with pulmonary tuberculosis were recruited from April 2005 to December 2006 in the Division of Pulmonology at the University of Cape Town with the following inclusion criteria: sputum smear positive for acid fast mycobacteria and culture positive for *Mycobacterium tuberculosis* sensitive to at least ¾ first-line drugs, bilateral cavitary tuberculosis on chest radiograph, and if HIV-1+, CD4+>200 cells/μL or CD4:CD8 ratio>0.3:1, and not on anti-retroviral therapy. Exclusion criteria included extrapulmonary tuberculosis, AIDS-defining opportunistic infection, or history of severe bronchospasm. We randomized 96 patients who met the entrance criteria. Four of these individuals grew Mtb (BACTEC method) resistant to both isoniazid and rifampin and were thus ineligible due to MDR-TB, two patients had negative cultures for Mtb, and one patient received a streptomycin-containing regimen. All of the remaining 89 patients had Mtb cultured from their sputum and were drug-sensitive. Respiratory and systemic symptoms were reviewed at baseline and weekly during treatment. IRB approval was obtained at NYU School of Medicine and the University of Cape Town. IFN-γ1b was nebulized with an AeroEclipse breath-activated nebulizer, or was administered subcutaneously.

Bronchoalveolar lavage was performed at baseline and 4 months. Briefly, after local anesthesia with lidocaine, the bronchoscope was inserted via the nasal passage to the lower respiratory tract and a 300-ml lavage was performed using 5, 20-ml aliquots of normal saline in each of three involved lung segments. The recovered fluid was filtered over sterile gauze, the volume recovered measured and a total cell count performed. A cytospin slide was stained with Diff-Quik and 500 cells counted to determine the cell differential. BAL supernatants were collected in RPMI over 24 hours at $10^6$ BAL cells/ml. Cytokines IL-1β, IL-6, IL-8, and IL-10 were measured by Luminex Beadlyte ELISA assay. Peripheral blood was obtained at time 0, 1 month, and 4 months for in vitro stimulation. An in vitro Stimulation Index evaluated peripheral CD4+ cell response to PPD stimulation over 5 days.

Prior to entry into the study, tuberculosis patients had a posterior-anterior and lateral chest x-ray to evaluate for the presence of cavities. At randomization and 4 months, each participant had a chest CT-scan at the Groote Schuur Hospital using a Somatom Balance apparatus (Siemens Medical, Ehrlangen, Germany) and a single breathhold technique. The collimator was set at 3 mm standard cuts from the superior margin of the clavicles to the adrenal glands. The standard reconstruction algorithm was used for soft tissue and high frequency filter for the lung. The internal volume of each cavity was assessed using internal cross-sectional diameters.

The analysis, which included all 89 randomized and eligible subjects, was performed according to the intention-to-treat principle. Summary statistics (mean, median, standard deviation, and frequency distribution) were generated for baseline demographics and clinical presentations to characterize the study population. To compare the baseline characteristics between 3 treatment groups, ANOVA was used for continuous variables, and Chi-square or Fisher's exact test, for categorical variables. The primary endpoint of the study was the time to smear conversion and culture conversion. Kaplan Meier curves were generated for the time to smear conversion by treatment groups. The Chi-square test was used to compare the percentage of subjects who had smear conversion before 4 weeks between treatment groups. To assure the quality of data, 6 subjects with zero or only one follow-up sputum smear sample were excluded from the analysis. The analysis of culture conversion was done in the same way. For the change of symptom at 4 weeks, we averaged the results from the 3rd, 4th and 5th week data for each subject, and used ANOVA and two sample t-test for 3 groups and two groups comparison, respectively. For the analysis of cell differentials in BAL, functional assays, and cavity sizes, paired t-test or Wilcoxon signed rank test was used to compare baseline and 16 weeks values in each treatment group, and ANOVA or Kruskal-Wallis test was used to compare the change from baseline to 16 weeks between treatment groups, as appropriate. All tests were two sided and p-values less than 5% were considered statistically significant. All analyses were conducted using SAS software.

Results. 96 patients were randomized, and 89 were eligible for the study. 12 patients did not complete the trial including 4 patients who were lost to follow-up, 2 who withdrew consent, and 6 who were withdrawn due to serious adverse events (SAE's) including 1 diabetic ketoacidosis, 2 hepatitis, 1 community acquired pneumonia, 1 hypoxia, and 1 died in a motor vehicle accident at 16 weeks. The SAE's were not thought to be treatment-related based on Data Safety Management Board review, although the hypoxia in the patient with emphysema occurred during bronchoscopy, and the procedure was terminated. They had been randomized to control DOTS, nebulized IFN-γ1b, and subcutaneous IFN-γ1b.

The mean age of the tuberculosis patients who were eligible for the study ranged from 32-35 years and did not differ among groups (Table 1). The 3 groups were closely matched for gender (63% to 81% male), and race (56-63% mixed) and symptoms. Eighty percent had a history of smoking. There were 6 patients who were co-infected with HIV-1 and their mean CD4+ was 253 cells/μL. At baseline, the three groups were comparable in respiratory and constitutional symptoms (Table 1).

TABLE 1

Baseline Table for Demographic Characteristics for the Three Arms.

|  | DOTS | NEBULIZED-IFN-γ | SUBCUTANEOUS-IFN-γ | p-value |
|---|---|---|---|---|
| N | 30 | 32 | 27 |  |
| Age | 32 +/− 11 | 34 +/− 10 | 35 +/− 13 | 0.55 |
| Gender |  |  |  |  |
| Female | 37% | 25% | 19% | 0.29 |
| Male | 63% | 75% | 81% |  |
| Race |  |  |  |  |
| Black | 37% | 41% | 37% | 0.73 |
| More than one | 63% | 56% | 63% |  |
| Asian/white | 0% | 3% | 0% |  |
| Cough | 96% | 100% | 100% | 0.64 |
| Dyspnea = (2, 3) | 93% | 94% | 92% | 0.83 |
| Fever | 46% | 35% | 42% | 0.69 |
| Poor Appetite | 29% | 45% | 50% | 0.24 |
| Wheeze | 68% | 58% | 54% | 0.55 |
| Weakness | 50% | 65% | 62% | 0.50 |

TABLE 1-continued

Baseline Table for Demographic Characteristics for the Three Arms.

|  | DOTS | NEBULIZED-IFN-γ | SUBCUTANEOUS-IFN-γ | p-value |
|---|---|---|---|---|
| Tiredness | 86% | 77% | 92% | 0.29 |
| Night sweats | 3.8 +/− 2.7 | 3.0 +/− 2.7 | 3.2 +/− 3.1 | 0.54 |
| Sputum Vol <10 ml | 29% | 16% | 12% | 0.25 |
| Weight | 54 +/− 9 | 56 +/− 10 | 55 +/− 7 | 0.71 |
| Culture Positive | 96% | 91% | 83% | 0.31 |
| HIV-1+ | 2 | 2 | 2 |  |

Figure 13:
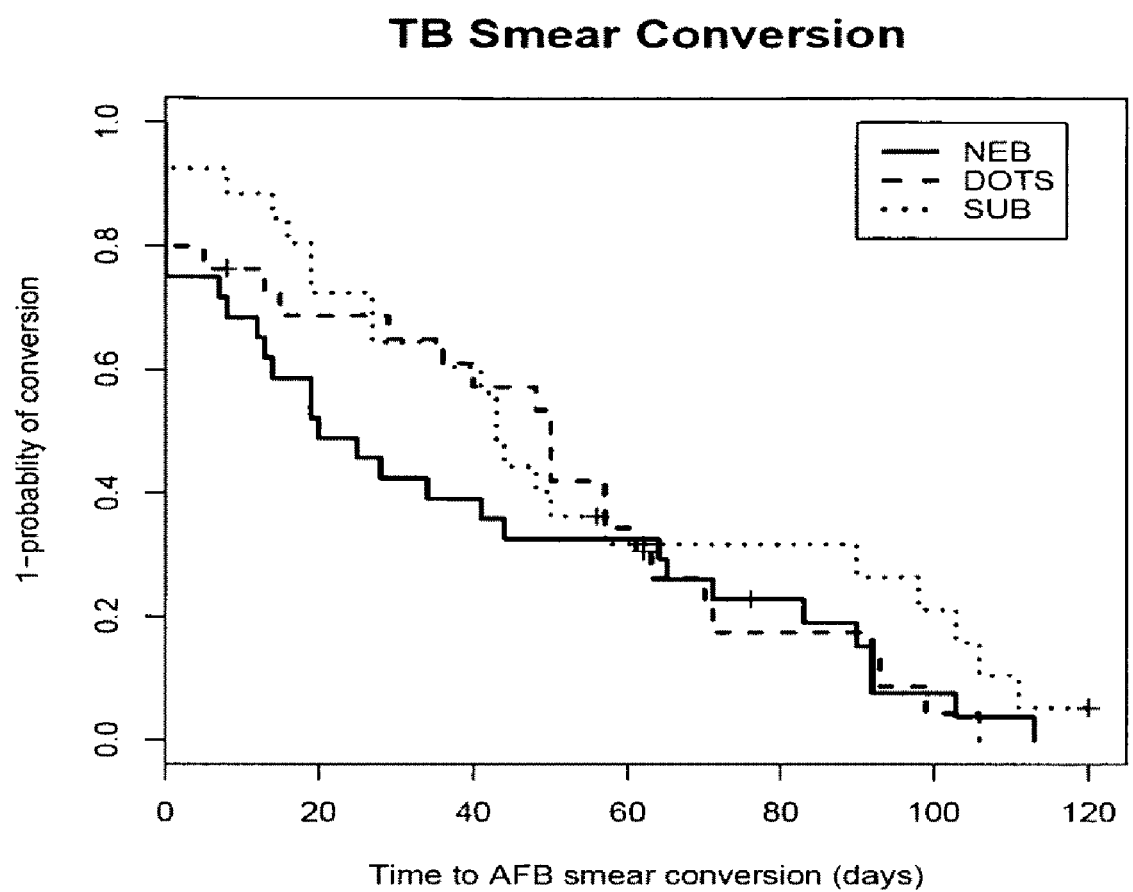
FIG. 13 represents *M tuberculosis* sputum smear conversion. At 4 weeks, there was a higher Mtb smear conversion rate in the NEB IFN-γ1b group compared to the other two treatment groups combined (p<0.05).
Figure 14:
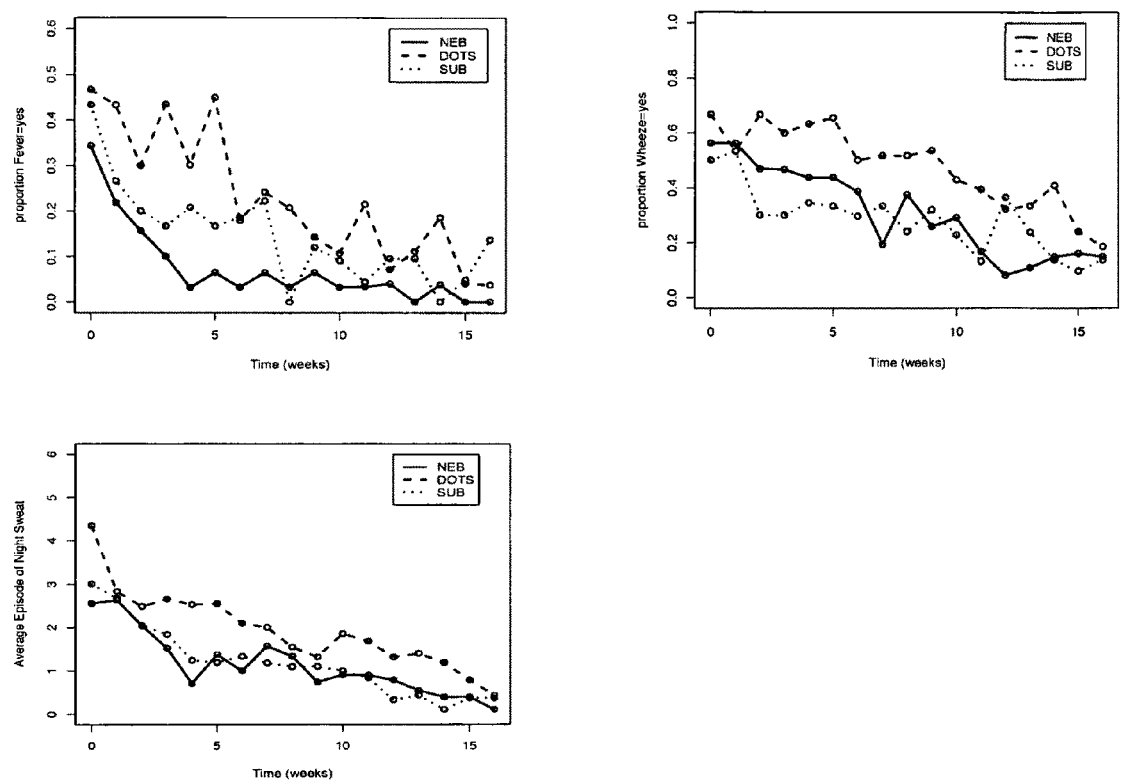
FIG. 14 represents the change in symptoms over 16 weeks comparing DOTS (dashed line) to DOTS plus IFN-γ1b groups (solid and dotted lines). A). IFN-γ1b significantly (p<0.05) reduced fever at 4 weeks. B). IFN-γ1b significantly reduced episodes of night sweats at 4 weeks. C). IFN-γ1b significantly reduced wheeze at 4 weeks. (All p<0.05).

At 4 weeks, there was a significantly higher smear conversion rate in the nebulized recombinant interferon-γ1b group compared to the other two treatment groups combined (60% versus 36%, p<0.05, FIG. 13). A trend towards higher culture conversion rate at 4 weeks was also observed in the nebulized group compared to the other two treatment groups (32% vs 18%, NS). There was a significant reduction in fever in the IFN-γ1b groups compared to control DOTS at 4 and 8 weeks (FIG. 14A, p<0.05). There also was a significant reduction in complaints of night sweats at 4 weeks in the IFN-γ1b groups (FIG. 14B, p<0.05). Also, there was a significant reduction in the proportion with wheeze in the IFN-γ1b groups at 4, 8, and 12 weeks (FIG. 14C, p<0.05). In addition, at 12 weeks there was a significant reduction in cough in the groups receiving IFN-γ1b. There was no statistically significant difference between treatment arms in the incidence of tiredness, poor appetite, sputum volume, or dyspnea.

There was a significant increase in median percent lymphocytes from baseline to 16 weeks in two of three groups in BAL (Table 2; DOTS 4% to 15%; IFN-γ1b-SC 6% to 22%; IFN-γ1b-NEB 5% to 15%, p<0.01 for DOTS and IFN-γ1b-SC). There was no change in lymphocytes/ml BALF recovered. There was a significant decrease in median percent neutrophils from baseline to 16 weeks in all three groups in BAL (Table 2; DOTS 28% to 11%; IFN-γ1b-SC 30% to 2%; IFN-γ1b-NEB 24% to 4%), and a remarkable decline in neutrophils/ml BALF recovered in all 3 groups (DOTS 3.98 to 0.30×$10^4$; IFN-γ1b-SC 3.59 to 0.23×$10^4$; IFN-γ1b-NEB 2.10 to 0.26×$10^4$). The percentage of macrophages increased slightly over the 16 weeks in all 3 groups. However, the macrophages/ml decreased 2-fold in all three groups (Table 2).

TABLE 2

Bronchoalveolar Lavage Results

|  | Week | DOTS | | | NEBULIZED-IFN-γ | |
|---|---|---|---|---|---|---|
|  |  | Lymphocytes | Macrophages | Neutrophils | Lymphocytes | Macrophages |
| % | Week 0 | 4 (2, 8) | 60 (17, 84) | 28 (10, 82) | 5 (3, 15) | 60 (32, 80) |
|  | Week 16 | 15 (6, 25) | 64 (44, 72) | 11 (3, 31) | 15 (8, 34) | 63 (40, 84) |
|  | p-value | <0.01 | 0.13 | 0.01 | 0.11 | 0.42 |
| Cells/ml (10e4) | Week 0 | 0.75 (0.26, 1.50) | 7.80 (2.58, 12.75) | 3.98 (0.96, 20.7) | 0.84 (0.30, 2.17) | 7.43 (4.80, 10.64) |
|  | Week 16 | 0.63 (0.40, 1.20) | 2.60 (1.98, 4.68) | 0.30 (0.12, 2.00) | 0.80 (0.52, 1.60) | 3.64 (1.98, 7.20) |
|  | p-value | 0.90 | 0.09 | <0.01 | 0.68 | 0.46 |

|  |  | NEBULIZED-IFN-γ | SUBCUTANEOUS-IFN-γ | | |
|---|---|---|---|---|---|
|  | Week | Neutrophils | Lymphocytes | Macrophages | Neutrophils |
| % | Week 0 | 24 (5, 56) | 6 (3, 10) | 62 (43, 83) | 30 (4, 54) |
|  | Week 16 | 4 (2, 16) | 22 (13, 33) | 66 (54, 77) | 2 (2, 9) |
|  | p-value | 0.05 | <0.01 | 0.94 | 0.02 |
| Cells/ml (10e4) | Week 0 | 2.10 (0.67, 11.20) | 0.56 (0.29, 1.86) | 7.26 (3.47, 17.76) | 3.59 (0.60, 13.60) |
|  | Week 16 | 0.26 (0.14, 0.82) | 1.32 (0.58, 3.22) | 3.63 (1.90, 6.50) | 0.23 (0.08, 0.52) |
|  | p-value | 0.04 | 0.09 | <0.01 | <0.01 |

* median

Figure 15:
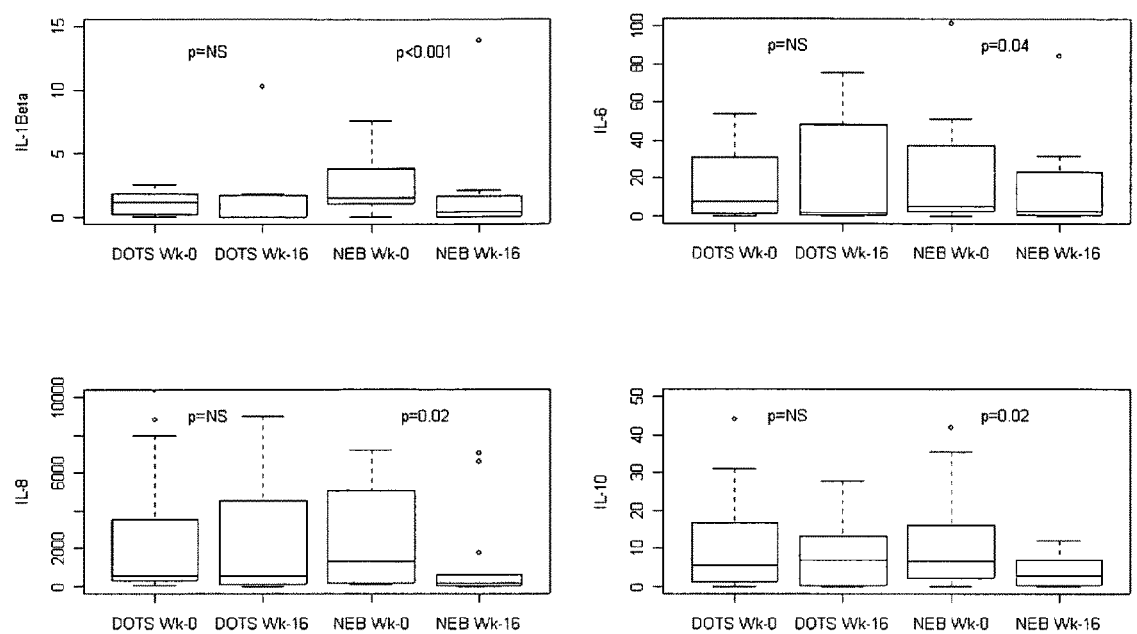
FIG. 15 represents reduction in inflammatory cytokines in 24 hour BAL supernatants by Nebulized IFN-γ1b comparing baseline to 16 weeks in ng/ml. A). IL-1β. DOTS vs. NEB IFN-γ1b plus DOTS, p<0.001. B). IL-6. DOTS vs. NEB IFN-γ1b plus DOTS, p<0.04. C). IL-8. DOTS vs. NEB IFN-γ1b plus DOTS, p<0.02. D). IL-10. DOTS vs. NEB IFN-γ1b plus DOTS, p<0.02.

There was a significant decline in inflammatory cytokines in 24 hour BAL supernatants in the nebulized IFN-γ1b group alone from baseline to week 16: IL-1β (p<0.001), IL-6 (p=0.04), IL-8 (p=0.02), and IL-10 (p=0.02) (FIG. 15). PBMCs collected at one month showed a significant increase in CD4+ proliferative response to PPD (DOTS alone 3.7±2.6, IFN-γ1b-SC 9.3±11.4, IFN-γ1b-NEB 9.1±7.4, p<0.01) suggesting a systemic response to both modes of administration. Proliferative responses by PBMC from all 3 groups to *Staphylococcus aureus* enterotoxin was 66-73-fold and mumps was 0.8 to 1.9 (NS for both tests).

There was a striking improvement in cavity size as assessed by HRCT in all 3 groups between baseline and 16 weeks; however, the IFN-γ1b groups did not differ from DOTS alone (Cavity in mm: DOTS 34+/−11 to 20+/−16; IFN-γ1b-SC 39+/−24 to 29+/−24; IFN-γ1b-NEB 34+/−13 to 18+/−17.

Discussion. Treatment of drug-sensitive pulmonary tuberculosis with nebulized IFN-γ1b as an adjunct cleared *M tuberculosis* from the sputum and resolved the classic symptoms of fever, night sweats, wheeze, cough and malaise more rapidly than treatment with either DOTS or DOTS plus subcutaneous IFN-γ1b. This finding suggests that nebulized IFN-γ1b reduces transmission of tuberculosis due to more rapid clearance of *M tuberculosis* during the first 4 weeks. Additionally, nebulized IFN-γ1b plus DOTS significantly reduced lung inflammatory cytokines in BAL supernatants at the 16 week time point. There was a recruitment of lymphocytes and reduction in the neutrophil inflammation in the lung in all three groups, which manifested clinically as a dramatic resolution of the macrophage-neutrophilic alveolitis in the lower respiratory tract. Concomitantly with the increase in BAL lymphocytes, blood CD4+ cells doubled in their proliferative capacity to PPD stimulation at the 4 week time point. All treatment groups experienced radiographic improvement with resolution of cavities by 16 weeks.

In summary, the addition of nebulized interferon-γ1b to DOTS in a randomized, controlled clinical trial resulted in more rapid clearance of Mtb from the sputum, improved symptoms, and reduced inflammatory macrophage-neutrophil alveolitis. These findings suggest that nebulized interferon-γ1b may have a role in the therapeutic management of patients with cavitary tuberculosis. Further studies are required to confirm these findings and determine the optimal dose and frequency of administration.

Example 6

*Mycobacterium tuberculosis* (Mtb) infects one-third of the world's population, resulting in 9.2 million active cases per year (Maartens, et al. (2007) *Lancet* 370: 2030-2043). Since the Directly Observed Therapy (Isoniazid, Rifampin, Pyrazinamide, Ethambutol 6 month Short Course, DOTS) approach is highly successful, the World Health Organization has set the goal of achieving 85% adherence, and the Global Plan to Stop TB has a vision of halving the prevalence and mortality of tuberculosis by 2015 (Young, et al. (2008) *J Clin Invest* 118: 1255-1265). Transgenic knockout models of mycobacteria-exposed mice demonstrate that interferon-γ and its signaling intermediates are critical to host defense (Flynn, et al. (1993) *J Exp Med* 178: 2249-2254; Kamijo, et al. (1993) *J Exp Med* 178: 1435-1440). In humans, mutational defects in the interferon-γ receptor, the cytokine IL-12, or antibodies to interferon-γ result in disseminated mycobacterial infection (Seneviratne, et al. (2007) *Thorax* 62: 97-99; Dorman, et al. (2004) *Lancet* 364: 2113-2121).

Sputum culture positive at two months, cavitation on chest radiography, being underweight, and bilateral pulmonary involvement increases the risk of treatment failure and/or relapse (Tuberculosis Trials Consortium (2002) *Lancet* 360: 528-534. Responses of whole blood PBMC to PPD and other mycobacterial antigens are reduced in active tuberculosis probably due to suppressor T cells (Tregs) or cytokines, e.g. IL-10 or TGF-β (Hirsch, et al. (1999) *J Infect Dis* 180: 2069-2073; Hougardy, et al. (2007) *Am J Respir Crit Care Med* 176: 409-416.) Bronchoalveolar lavage (BAL) of patients with pulmonary tuberculosis has shown increases in inflammatory cytokines and percent CD4+ cells compared to uninfected controls, and in advanced, cavitary tuberculosis markers of effective immunity are reduced. Nitric oxide (NO) has been identified as a mechanism of mycobacterial killing, while mycobacteria can also be eliminated by autophagy, apoptosis, cytotoxic CD8+ cells, alpha defensins from neutrophils, and phagosomal-lysosomal rupture with subsequent cytosolic demise (Martineau, et al. (2007) *J Clin Invest* 117: 1988-1994; Van der Wel, et al. (2007) *Cell* 129: 1287-1298; Gutierez, et al. (2004) *Cell* 119: 753-766). However, mycobacteria have evolved virulence factors to persist in macrophages, possibly disrupting the interferon-γ signaling pathways. We hypothesized that pharmacologic doses of rIFN-γ1b could augment the host immune response in TB, and to evaluate this we conducted a 4-month randomized, controlled clinical trial with rIFN-γ1b at 200 µg/day for three days/week with three arms: nebulized rIFN-γ1b or subcutaneous rIFN-γ1b with DOTS versus DOTS alone. End points were: BAL cytokine release, treatment failure, sputum smear and culture conversion, and respiratory and systemic symptoms. We evaluated BAL cytokines, mycobacterial and clinical response, immunological outcomes, and postulate mechanisms that rIFN-γ1b augmented to achieve an improved outcome.

Materials and Methods

Study Subjects

Patients with pulmonary tuberculosis were recruited from April 2005 to December 2006 in the Division of Pulmonology at the University of Cape Town with the following inclusion criteria: sputum smear and culture positive for *Mycobacterium tuberculosis*, and bilateral cavitary tuberculosis. We randomized 96 patients who met the entrance criteria. Four of these individuals grew Mtb (BACTEC method) resistant to both isoniazid and rifampin and were thus ineligible due to MDR-TB, two patients had negative cultures for Mtb, and one patient had received a streptomycin-containing regimen. They had been randomized with 4 subjects in the DOTS plus subcutaneous IFN-γ, 2 in the DOTS alone group, and 1 in the DOTS plus nebulized IFN-γ group. All of the remaining 89 patients had Mtb cultured from their sputum and were drug-sensitive. Respiratory symptoms (cough, wheeze, dyspnea grade 2 or 3, sputum volume <10 ml) and night sweats (number/week) were reviewed at baseline and weekly during treatment by a blinded interviewer; oral temperature (fever defined as 38.5° C.) was recorded by the study nurse 3 times/week. IRB approval was obtained at NYU School of Medicine and the University of Cape Town; all study subjects signed informed consent in their native language. rIFN-γ1b (recombinant, InterMune Brisbane, Calif.) was nebulized with an AeroEclipse breath-activated nebulizer (which improves alveolar deposition), or was administered subcutaneously at 200 micrograms (excipient normal saline) three times per week over 4 months. All patients had weekly sputum smear and culture to 4 months and were followed up at 12 months with sputum smear and culture.

Bronchoalveolar Lavage

Bronchoalveolar lavage was performed at baseline and 4 months. Briefly, after local anesthesia with lidocaine, the bronchoscope was inserted via the nasal passage to the lower respiratory tract, wedged, and a 300-ml lavage was performed using 5, 20-ml aliquots of normal saline in each of three involved lung segments. The recovered fluid was pooled and filtered over sterile gauze, and a total cell count performed. A cytospin slide was stained with Diff-Quik and 500 cells counted to determine the cell differential. BAL supernatants were collected in RPMI over 24 hours at $10^6$ BAL cells/ml. Cytokines IL-1β, IL-6, IL-8, TNF-α, and IL-10 were measured by Luminex Beadlyte ELISA assay. Immunoblots for C/EBPβ were done as previously described (Condos, et al. (1997) *Lancet* 349: 1513-1515; Condos, et al. (2003) *Infect Immun* 71: 2058-2064; Nicholson, et al., (1996) J Exp Med 183: 2293-2302).

Systemic Response

Peripheral blood was obtained between 3-5 weeks for in vitro stimulation. Mononuclear cells (PBMC) isolated by Ficoll-Paque were cultured for 5 days in the absence or presence of staphylococcal enterotoxin B, Mumps antigen, or PPD and pulsed with BrDU during the last 24 hr. Cells were labeled with PerCP-Cy5.5-anti-CD4 and allophycocyanin-anti-CD25, fixed and permeabilized, then labeled with FITC-anti-BrDU in the presence of DNase I. Labeled cells were analyzed on a FACSCalibur, and lymphoblasts displaying PerCP-Cy5.5 were identified as CD4+. Proliferating cells were detected as CD25+ BrDU+ lymphoblasts. The proliferation index is given by the % CD25+ BrDU+lymphoblasts normalized by the % lymphoblast-sized cells in the CD4+ population in each culture.

Radiographic Studies

Prior to entry into the study, tuberculosis patients had to have a posterior-anterior and lateral chest x-ray to evaluate for the presence of cavities. At randomization and 4 months, each participant had a chest CT-scan at the Groote Schuur Hospital using a Somatom Balance apparatus (Siemens Medical, Ehrlangen, Germany) and a single breathhold technique. The collimator was set at 3 mm standard cuts from the superior margin of the clavicles to the adrenal glands. The standard reconstruction algorithm was used for soft tissue and high frequency filter for the lung. The internal volume of each cavity was assessed using internal cross-sectional diameters.

Statistical Analysis

The analysis, which included all 89 randomized and eligible subjects, was performed according to the intention-to-treat principle. Summary statistics (mean, median, standard deviation, and frequency distribution) were generated for baseline demographics and clinical presentations to characterize the study population. To compare the baseline characteristics between 3 treatment groups, one-way ANOVA or Kruskal-Wallis test was used for continuous variables, and Chi-square or Fisher's exact tests, for categorical variables (Table 3). The primary endpoint of the study was the time to smear conversion and culture conversion. Kaplan Meier curves were generated for the time to smear conversion by treatment groups. The log-rank test was used to compare the Kaplan Meier curves before 4 weeks. The analysis of culture conversion was done in the same way. For the change of symptom at 4 weeks, we averaged the results from the 3rd, 4th and 5th week data for each subject, and used one-way ANOVA and two sample t-test for 3 group and two group comparisons, respectively. For the analysis of cell differentials in BAL, functional assays, and cavity sizes, the paired t-test or Wilcoxon signed rank test was used to evaluate the change from baseline to 16 weeks within each treatment group (Table 4), and one-way ANOVA or Kruskal-Wallis test was used to compare the change from baseline to 16 weeks between treatment groups, as appropriate (Table 5). No adjustment for multiple comparisons was used and no missing data were imputed. All tests were two sided and p-values less than 5% were considered statistically significant. All analyses were conducted using SAS software.

Demographics

Figure 16:
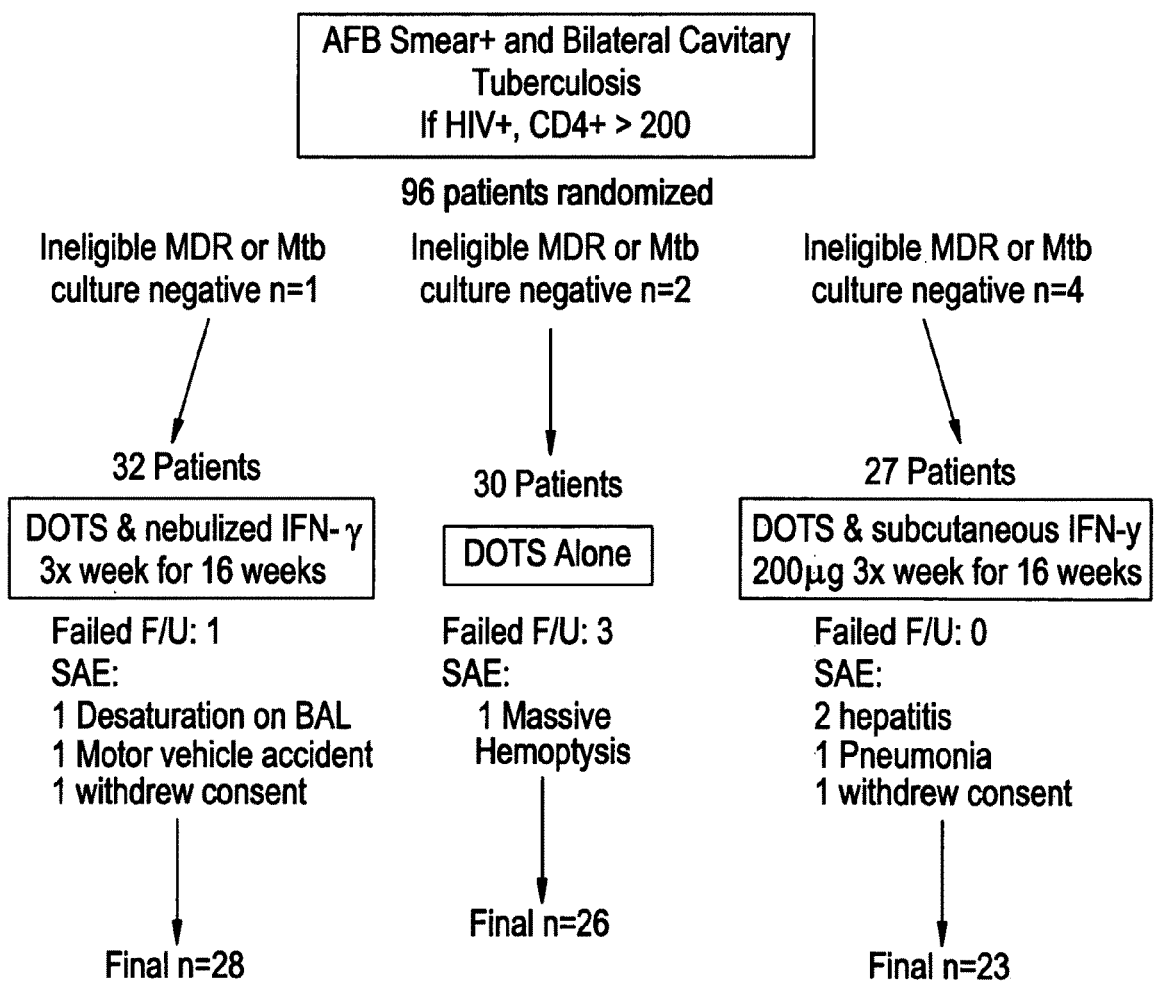
FIG. 16 provides a flow diagram showing number of study subjects screened, randomized to the three study groups n=96, and who met inclusion criteria, n=89).

There were 96 patients who were randomized and 89 who were eligible for the study. 10 patients did not complete the trial including 4 patients who were lost to follow-up, 2 who withdrew consent, and 4 who were withdrawn due to serious adverse events (SAE's): 2 hepatitis, 1 community acquired pneumonia, 1 hypoxia. Also 1 died from massive hemoptysis, and 1 died in a domestic accident (the SAE occurred after 16 weeks but before the end of their DOTS so were left in the analysis, FIG. 16). The SAE's were not thought to be treatment-related based on Data Safety Management Board review although the hypoxia in the patient with emphysema occurred during the bronchoscopy and the procedure was terminated.

The mean age of the tuberculosis patients who were eligible for the study ranged from 32-35 years and did not differ among groups (Table 3). The 3 groups were closely matched for gender (63% to 81% male), and race (56-63% mixed) and symptoms. Eighty percent had a history of smoking. There were 6 patients who were co-infected with HIV-1 and their mean CD4+ was 253 cells/μL (all with CD4+>200 and randomized to DOTS 2, DOTS plus subcutaneous 1 and nebulized 3. At baseline, the three groups were comparable in respiratory and constitutional symptoms (Table 3).

Bronchoalveolar Lavage

There was a significant increase in median percent lymphocytes from baseline to 16 weeks in two of three groups in BAL (Table 2; DOTS 4% to 15%; rIFN-γ1b-SC 6% to 22%; rIFN-γ1b-NEB 5% to 15%, p<0.01 for DOTS and rIFN-γ1b-SC). There was no change in lymphocytes/ml BALF recovered. There was a significant decrease in median percent neutrophils from baseline to 16 weeks in all three groups in BAL (Table 2; DOTS 28% to 11%; rIFN-γ1b-SC 30% to 2%; rIFN-γ1b-NEB 24% to 4%), and a remarkable decline in neutrophils/ml BALF recovered in all 3 groups (DOTS 3.98 to $0.30 \times 10^4$; rIFN-γ1b-SC 3.59 to $0.23 \times 10^4$; rIFN-γ1b-NEB 2.10 to $0.26 \times 10^4$). The percentage of macrophages increased slightly over the 16 weeks in all 3 groups. However, the macrophages/ml decreased 2-fold in all three groups (Table 4).

TABLE 3

Baseline Table for Demographic Characteristics for the Three Arms.

| | DOTS | NEBULIZED-rIFN-c | SUBCUTANEOUS-rIFN-c | p-value |
|---|---|---|---|---|
| N | 30 | 32 | 27 | |
| Age years+/2SD | 32+/211 | 34+/210 | 35+/213 | 0.55 |
| Gender | | | | |
| Female | 37% | 25% | 19% | 0.29 |
| Male | 63% | 75% | 81% | |
| Race | | | | |
| Black | 37% | 41% | 37% | 0.73 |
| More than one | 63% | 56% | 63% | |
| Asian/White | 0% | 3% | 0% | |
| Cough | 96% | 100% | 100% | 0.64 |
| Dyspnea = (2, 3) | 93% | 94% | 92% | 0.83 |
| Fever (oral T) | 46% | 35% | 42% | 0.69 |
| Poor Appetite | 29% | 45% | 50% | 0.24 |
| Wheeze | 68% | 58% | 54% | 0.55 |
| Weakness | 50% | 65% | 62% | 0.50 |
| Tiredness | 86% | 77% | 92% | 0.29 |
| Night Sweats (Nights/week) | 3.8+/22.7 | 3.0+/22.7 | 3.2+/23.1 | 0.54 |
| Sputum Vol. 10 ml | 29% | 16% | 12% | 0.25 |
| Weight Kg+/2SD | 54+/29 | 56 + 210 | 55+/27 | 0.71 |

TABLE 4

Bronchoalveolar Lavage Results

| DOTS | % | | | Cells BAL Recovered (10e4) | | |
|---|---|---|---|---|---|---|
| | Lymphocytes | Macrophages | Neutrophils | Lymphocytes | Macrophages | Neutrophils |
| Week 0 | 4 (2.8) | 60 (17.84) | 28 (10.82) | 0.75 (0.26, 1.50) | 7.80 (2.58, 12.75) | 3.98 (0.96, 20.7) |
| Week 16 | 15 (6.25) | 64 (44.72) | 11 (3.31) | 0.63 (0.40, 1.20) | 2.60 (1.98, 4.68) | 0.03 (0.12, 2.00) |
| p-value | 0.01 | 0.13 | 0.01 | 0.90 | 0.09 | 0.01 |
| NEBULIZED r-IFN-c | | | | | | |
| Week 0 | 5 (3.15) | 60 (32.80) | 24 (5.56) | 0.84 (0.30, 2.17) | 7.43 (4.80, 10.64) | 2.10 (0.67, 11.20) |
| Week 16 | 15 (8.34) | 63 (40.84) | 4 (2.16) | 0.80 (0.52, 1.60) | 3.64 (1.98, 7.20) | 0.26 (0.14, 0.82) |
| p-value | 0.11 | 0.42 | 0.05 | 0.68 | 0.46 | 0.04 |
| SUBCUTANEOUS rIFN-c | | | | | | |
| Week 0 | 6 (3.10) | 62 (43.83) | 30 (4.54) | 0.56 (0.29, 1.86) | 7.26 (3.47, 17.76) | 3.59 (0.60, 13.60) |
| Week 16 | 22 (13.33) | 66 (54.77) | 2 (2.9) | 1.32 (0.58, 3.22) | 3.63 (1.90, 6.50) | 0.23 (0.08, 0.52) |
| p-value | 0.01 | 0.94 | 0.02 | 0.09 | 0.01 | 0.01 |

Median (25-75 percentile)

Functional Assays

Figure 17:
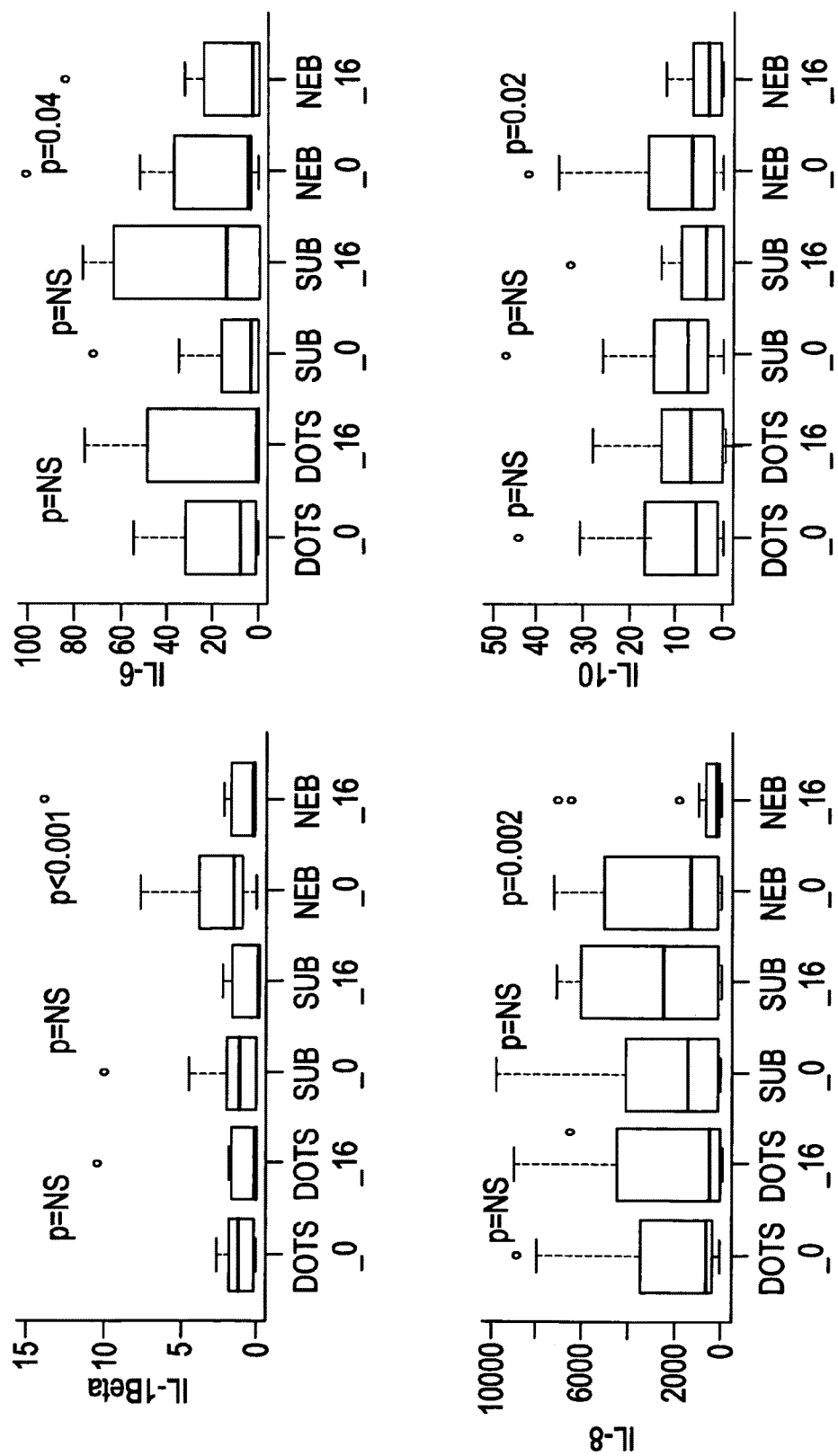
FIG. 17 demonstrates reduction in inflammatory cytokines in 24 hour BAL supernatants by nebulized rIFN-γ1b comparing baseline to 16 weeks in ng/ml.
A). IL-1β. DOTS or SC rIFN-γ plus DOTS, NS; NEB rIFN-γ1b plus DOTS, p<0.001. B). IL-6. DOTS or SC rIFN-γ plus DOTS, NS; NEB rIFN-γ1b plus DOTS, p<0.04. C). IL-8. DOTS or SC rIFN-γ plus DOTS, NS; NEB rIFN-γ1b plus DOTS, p<0.02. D). IL-10. DOTS or rIFN-γ plus DOTS, NS; NEB rIFN-γ1b plus DOTS, p<0.02.

There was a significant decline in inflammatory cytokines in 24 hour BAL supernatants in the nebulized rIFN-γ1b group only from baseline to week 16: IL-1β (p<0.001), IL-6 (p=0.04), IL-8 (p=0.02), and IL-10 (p=0.02) (FIG. 17).

Figure 18B:
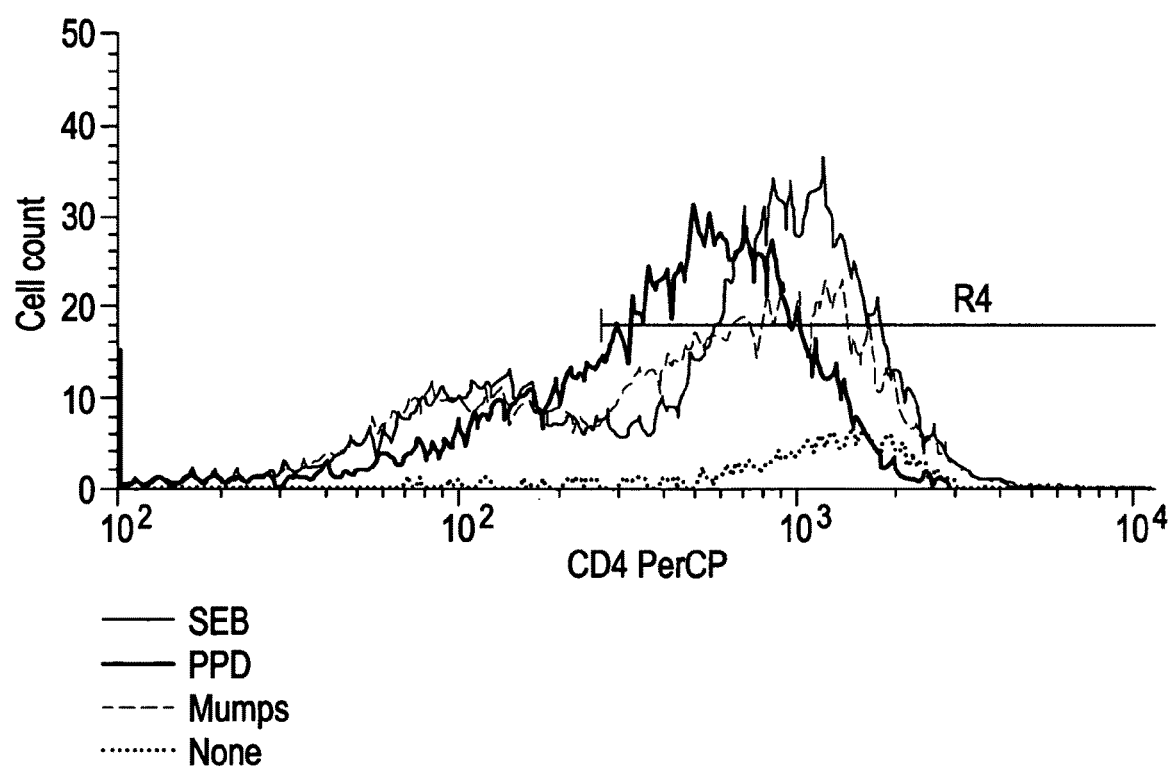
FIG. 18 demonstrates detection of the CD4+ proliferative response from a representative patient. Peripheral blood mononuclear cells were cultured for 5 days, and pulsed with BrDU during the last 24 hr. Viable cells were labeled with PerCP-anti-CD4 and PE-anti-CD25, permeabilized and reacted with FITC-anti-BrDU in the presence of DNase, fixed and analyzed by FACS. (A) Lymphoblasts [R2] were discriminated from resting lymphocytes [R1] by forward and 90° angle (side) scattered laser light. Debris and necrotic cells are indicated by arrowheads. % lymphoblasts were given by the number of R2 cells divided by the number of R1+R2 cells. Approximately 10,000 events are shown in each dot blot. (B) CD4 intensity on R2 cells [R4] was used to select for CD4+ lymphoblasts. (C) Proliferating lymphoblasts which are displayed as green dots in (A). A total of 600
Figure 18C:
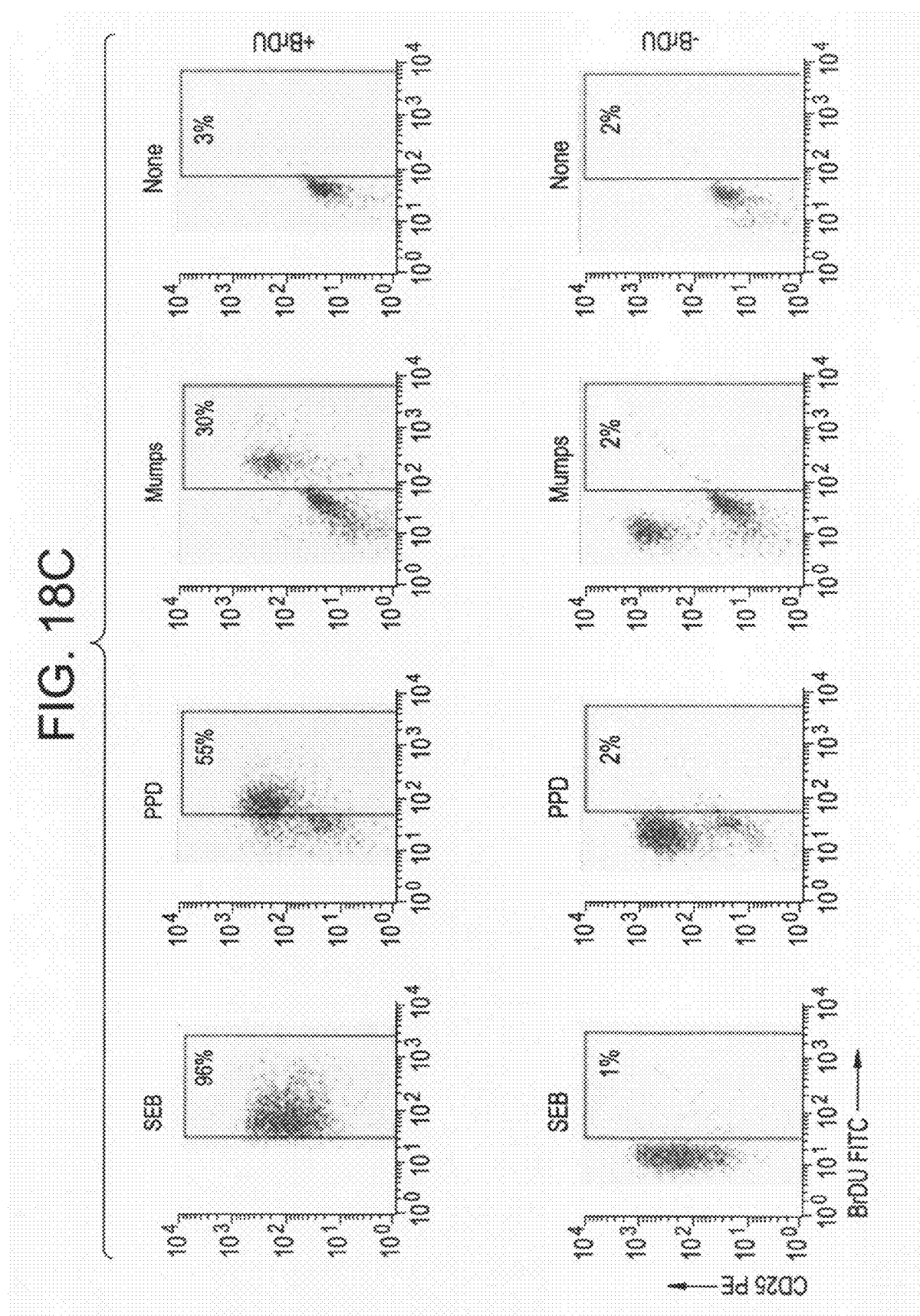

Peripheral blood lymphocytes showed a significant 2.8-fold increase in Th1 proliferation when stimulated with PPD but not SEB or MUMPS in vitro (FIG. 18 and Table 5), demonstrating an enhanced antigen-specific systemic response after one month of both nebulized and subcutaneous rIFN-γ1b administration.

TABLE 5

Proliferative Indices of CD4+ Peripheral Blood Lymphocytes from Cavitry TB Patients after 3-5 Weeks of Treatment

| Treatment | N | SEB | MUMPS | PPD |
|---|---|---|---|---|
| DOTS alone | 17 | 7.02 63.4 | 1.6 61.1 | 3.2 60.6 |
| Dots + Nebulized INF-c | 19 | 6.88 64.8 | 0.7 60.2 | 9.1 62.6 |
| p, DOTS vs DOTS + Nebulized INF-c | | 0.825 | 0.475 | 0.041 |
| Dots + Subcutaneous IFN-c | 18 | 65.9 63.0 | 0.7 60.2 | 9.1 62.2 |
| p, DOTS vs DOTS + Subcutaneous IFN-c | | 0.359 | 0.444 | 0.017 |

Proliferation indices (mean 6SEM) were determined by flow cytometry following in vitro stimulation for 5 days with a T cell mitogen (SEB), Mumps antigen, or PPD at pretitered concentrations. Values given are those determined in the presence of antigen less that determined in the absence of antigen was 0.2 60.4 for all specimens (N=54). Significance p was determined using unpaired t tests at 95% confidence interval.

Chest Radiology

There was a striking improvement in cavity size as assessed by HRCT in all 3 groups between baseline and 16 weeks; however, the rIFN-γ1b groups did not differ from DOTS alone (Cavity in mm: DOTS 34+/−11 to 20+/−16; rIFN-γ1b-SC 39+/−24 to 29+/−24; rIFN-γ1b-NEB 34+/−13 to 18+/−17.

Sputum Smear Conversion and Change in Symptoms

Figure 19A:
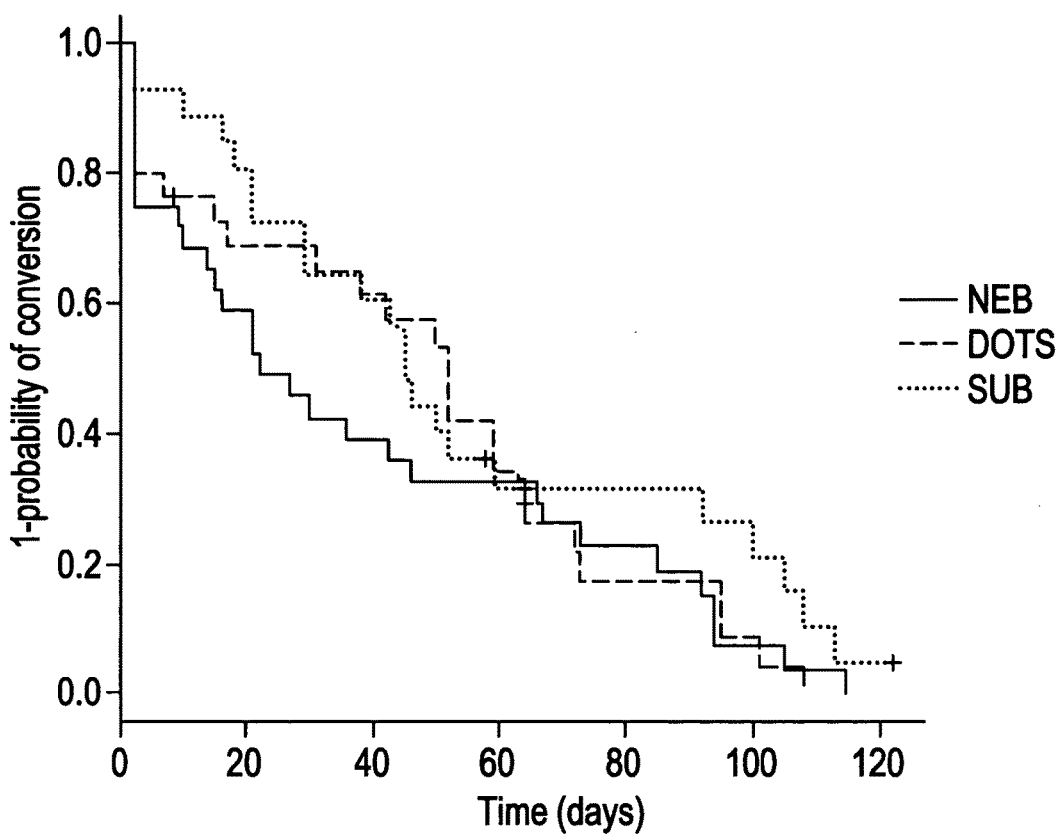
FIG. 19 demonstrates A. *M tuberculosis* sputum smear conversion. At 4 weeks, there was a higher Mtb smear conversion rate in the NEB rIFN-γ1b group compared to DOTS and subcutaneous IFN-γ1b plus DOTS (p=0.03). At enrollment, all sputa were Mtb smear and culture positive. Y axis represents 1—probability of conversion in a Kaplan-Meier curve. B. Change in fever over 16 weeks comparing DOTS (dashed line) to DOTS plus nebulized rIFN-γ1b group (solid line). rIFN-γ1b significantly (p<0.05) reduced subjective fever at 4 weeks. Y axis represents proportion of patients having fever.
Figure 19B:
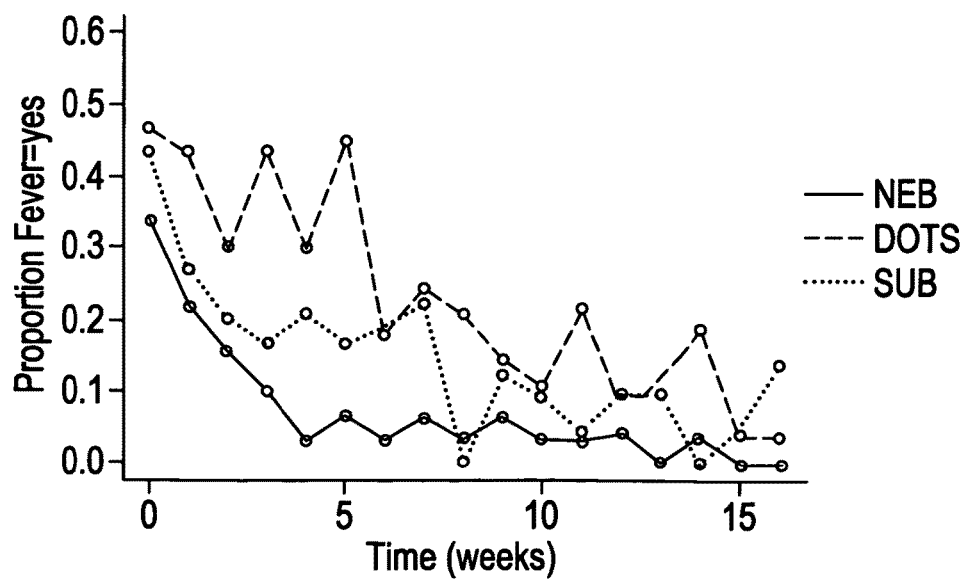

At 4 weeks, there was a significantly higher smear conversion rate in the nebulized rIFN-γ1b group compared to the DOTS control and subcutaneous rIFN-γ1b plus DOTS groups (60% versus 36% at 4 weeks, p=0.03 for comparing Kaplan-Meier curves before 4 weeks, FIG. 19A). A higher culture conversion rate at 4 weeks was also observed in the nebulized group compared to DOTS control and subcutaneous rIFN-γ1b plus DOTS (32% vs 18% at 4 weeks, p=0.15). There was a significant reduction in fever in both rIFN-γ1b groups compared to control DOTS at 4 and 8 weeks (FIG. 19B) and complaints of night sweats at 4 weeks in both rIFN-γ1b groups compared to DOTS control. Also, there was a significant reduction in the proportion with wheeze in both IFN-γ1b groups at 4, 8, and 12 weeks compared to DOTS control. In addition, at 12 weeks there was a significant reduction in cough in the groups receiving rIFN-γ1b compared to DOTS control. There was no statistically significant difference between treatment arms in the incidence of tiredness, poor appetite, sputum volume, or dyspnea. There was one treatment failure at 12 months in the DOTS alone group.

Reduction in the Number of Infectious Organisms and Infectivity

Immunoadjunctive therapy with nebulized rIFN-γ1b plus DOTS significantly reduced lung inflammatory cytokines in BAL supernatants at the 16 week time point. We treated five multiple-drug resistant tuberculosis patients with nebulized rIFN-γ1b while continuing their failing second-line regimens at a dose of 500 μg three times weekly for four weeks (Condos, et al. (1997) Lancet 349: 1513-1515). In all five patients, the sputum converted to negative, and symptoms improved. In order to investigate the mechanisms of these responses, we used nebulized rIFN-γ1b in eleven drug-sensitive tuberculosis patients, and found an increase in signaling molecules STAT-1, IRF-1 and IRF-9 (Condos, et al. (2003) Infect Immun 71: 2058-2064). In addition, nebulized rIFN-γ1b induced IP-10 downstream from these signaling molecules, but not inducible nitric oxide synthase (iNOS) (Nicholson, et al. (1996) J Exp Med 183: 2293-2302). There was a recruitment of lymphocytes and reduction in the neutrophil inflammation in the lung in all three groups, which manifested clinically as a dramatic resolution of the macrophage-neutrophilic alveolitis in the lower respiratory tract. Concomitantly with the increase in BAL lymphocytes, blood CD4+ cells doubled in their proliferative capacity to PPD or Mtb culture filtrate protein stimulation (data not shown) at the 4 week time point in both immunoadjunctive rIFN-γ1b groups of drug-sensitive pulmonary tuberculosis.

Immunoadjunctive therapy cleared *M tuberculosis* from the sputum and resolved the classic symptoms of fever, night sweats, wheeze, cough and malaise more rapidly than treatment with either DOTS or DOTS plus subcutaneous rIFN-γ1b. This finding suggests that nebulized rIFN-γ1b could reduce transmission due to more rapid clearance of *M tuberculosis* during the first 4 weeks. The subcutaneous rIFN-γ1b plus DOTS was not different from control since only nebulized rIFN-γ reaches the lower respiratory tract in pharmacological amounts to have a biological effect. All treatment groups experienced radiographic improvement with resolution of cavities by 16 weeks. Limitations of the study include the fact that this was an open-label, unblinded study without a placebo, and there was no group with rIFN-γ1b alone.

At 12 months there was only one study subject who had a treatment failure with culture positive sputum, and this occurred in the DOTS only control arm. TB Trials Consortium Study 22 comparing rifapentene and isoniazid once a week versus rifampicin and isoniazid twice a week reported bilateral pulmonary involvement and cavitation on chest radiograph were two risk factors (out of five) for treatment failure/relapse that occurred in 74/1004 (14.9%) of the TB patients (Tuberculosis Trials Consortium (2002) *Lancet* 360: 528-534). Although our numbers were much smaller, we had no treatment failures/relapses among the adjunctive rIFN-γ1b groups.

This is the first major report on the efficacy of rIFN-γ1b in a randomized clinical trial. In the first study of nebulized versus subcutaneous rIFN-γ in humans, IP-10 mRNA was detected in BAL cells only in the nebulized patients and not subcutaneous rIFN-γ treated subjects (Jaffe, et al. (1991) *J Clin Invest* 88: 297-302). This probably explains the finding that only nebulized rIFN-γ1b and not subcutaneous rIFN-γ1b was successful in clearing the sputum of Mtb and reducing the spontaneous release of inflammatory cytokines in 24 hour BAL supernatants. A pilot study of intramuscular rIFN-γ plus second-line anti-TB drugs over a 6-month period in 8 MDR-TB patients from Cuba showed sputum conversion over 1-3 months and marked improvement of radiographic abnormalities (Suárez-Méndez, et al. (2004) *BMC Infect Dis* 4: 44). Giosue and colleagues nebulized IFN-α, a type I interferon, for 2 months as an adjunct in a randomized controlled clinical trial in 20 drug sensitive tuberculosis patients (Giosuè, et al. (1998) *Am J Respir Crit Care Med* 158: 1156-1162). Improvements in Mtb number in the sputum at 7 days, reduced fever by 7 days, reduced number of nodules and area of consolidation on CT-scans at 2 months, and significant decreases in BAL fluid amounts at 2 months of IL-1β, IL-6, and TNF-α were noted in the IFN-α group Giosuè, et al. (1998) *Am J Respir Crit Care Med* 158: 1156-1162). In a clinical trial of interleukin-2 adjunctive therapy performed in Uganda, 110 TB patients were randomized to IL-2 subcutaneously twice/day for the first 30 days in addition to DOTS versus DOTS alone. Seventeen percent versus 30% sputum conversion, respectively, was observed at 4 weeks (Johnson, et al. (2003) *Am J Respir Crit Care Med* 168: 185-191). Tramontana and colleagues conducted a clinical trial of thalidomide in TB patients blocking TNF-α leading to enhanced weight gain and increased serum IFN-γ in vivo (Tramontana, et al. (1995) *Mol Med* 1: 384-397).

Microarray analyses of BAL cells from TB patients shows elevated cytokine IL-1β, adhesion molecule ICAM, TGF-β, apoptosis genes, and IFN-γ pathway genes (Grassi, et al. (2006) *Clin Immunol* 121: 100-107). Immunohistochemistry of Mtb-laden lungs show increased IFN-γ, IL-12, IP-10, and TGF-β in granulomas and areas with pneumonitis with reductions in IL-10 and IL-4 compared to controls (Bai, et al. (2004) *Tuberculosis* 84: 375-385). BAL in Brazilian TB patients shows increased mRNA for TGF-βRI and II and IL-10 with increased protein for IFN-γ, IL-10, and bioactive TGF-β suggesting that TB has both stimulatory and counter-regulatory molecules that may ultimately down-regulate the Th1 response (Bonecini-Almeida, et al. (2004) *Infect Immun* 72: 2628-2634). Th2 cytokines may be inhibited by antagonists such as IL-4δ2 that may be increased in TB (Dheda, et al. (2007) *Tuberculosis* 87: 237-241). PBMC responses from TB patients to Mtb in vitro are reduced, probably due to IL-10 which was increased in BAL cell supernatants. Gold and colleagues have reported low levels of Surfactant Protein A in BAL from involved segments of active TB along with increased IL-6, and reduced inhibitory C/EBPβ (Gold, et al. (2004) *Infect Immun* 72: 645-650).

BAL lymphocytes increased in all three groups after 4 months of therapy. Mtb is suppressive of the T cell immune response, e.g. IFN-γ response to PPD-stimulated PBMC is depressed and TGF-β and IL-10 are increased at the beginning of TB treatment and return to normal levels only at the end of treatment 6-9 months later (MacMicking, et al. (2003) *Science* 02: 654-659; Lienhardt, et al. (2002) *Eur J Immunol* 32: 1605-1613). In Gambian TB patients, T cell response to PPD from blood or pleural fluid was impaired pre-treatment, that changed to IFN-γ release after successful treatment or IL-4 after treatment failure; addition of IFN-α or IL-12 in vitro pre-treatment could alter the response to Th1 suggesting that immunotherapy could increase host defense against mycobacteria (Marchant, et al. (2001) *Am J Respir Cell Mol Biol* 24: 187-194). Significantly increased PBMC proliferative capacity to PPD in the nebulized and subcutaneous rIFN-γ1b groups occurred within 3-5 weeks of immunoadjunctive therapy.

Inflammatory cytokines IL-1β, IL-6, IL-8, IFN-γ and TNF-α as well as anti-inflammatory cytokines IL-10 and TGF-β (and its TGF-βRI and RII) are elevated in BAL from active TB patients (Toossi (2000) *Archivum Immunologiae et Therapiae Experimentalis* 48: 513-519). The inflammatory response in the lung in TB may include an increase in neutrophils, particularly in radiographically abnormal areas. Zhang and colleagues have previously reported that Mtb and its cell wall components stimulated IL-8 protein release and mRNA expression in vitro from alveolar macrophages (Zhang, et al. (1995) *J Clin Invest* 95: 586-592). In summary, the addition of nebulized recombinant interferon-γ1b to DOTS in a randomized, controlled clinical trial resulted in reduced BAL cytokines, more rapid clearance of Mtb from the sputum, improved symptoms, and reduced inflammatory macrophage-neutrophil alveolitis. These findings suggest that nebulized recombinant interferon-γ1b may have a role in adjunctive immune stimulation in patients with cavitary tuberculosis.

We claim:

1. A method for treating tuberculosis in a subject comprising administering 10-1000 μg of an aerosolized interferon-γ resulting in deposition of a therapeutically effective amount of interferon-γ in the periphery of the lungs of the subject.

2. The method of claim 1, wherein the tuberculosis improves as measured by an indication selected from the group consisting of a decrease in fever, a reduction in sputum production, a reduction in wheezing and a reduction in conversion of sputum cultures.

3. The method of claim 1, wherein the subject suffering from the tuberculosis is unresponsive to treatment with one or more antibiotics.

4. The method of claim 1, wherein the tuberculosis is multiple drug resistant (MDR-TB).

5. The method of claim 1, wherein aerosolized interferon-γ is administered at a dose ranging from about 100 to 750 μg at least three times per week.

6. The method of claim 1, wherein aerosolized interferon-γ is administered as a dose of about 200 μg at least three times per week.

7. The method of claim 1, wherein the amount of aerosolized interferon-γ administered is calculated and optimized.

8. The method of claim 1, wherein said administering results in improvement in pulmonary function tests.

9. A method of treating a patient having tuberculosis comprising delivering 10-1000 μg of an aerosolized interferon-γ in combination with a therapeutically effective amount of an antibiotic agent resulting in deposition of a therapeutically effective amount of interferon in the periphery of the lungs of the patient.

10. The method of claim 9, wherein the antibiotic agent is selected from the group consisting of isoniazid and rifampin.

11. The method of claim 9, wherein the tuberculosis improves as measured by an indication selected from the group consisting of a decrease in fever, a reduction in sputum production, a reduction in wheezing and a reduction in conversion of sputum cultures.

12. The method of claim 9, wherein the subject suffering from tuberculosis is unresponsive to treatment with one or more antibiotics.

13. The method of claim 9, wherein the tuberculosis is multiple drug resistant (MDR-TB).

14. The method of claim 9, wherein aerosolized interferon-γ is administered at a dose ranging from about 100 to 750μg at least three times per week.

15. The method of claim 9, wherein aerosolized interferon-γ is administered as a dose of about 200 μg at least three times per week.

16. The method of claim 9, wherein the amount of aerosolized interferon-γ administered is calculated and optimized.

17. The method of claim 9, wherein said administering results in improvement in pulmonary function tests.

18. A method for reducing the severity of tuberculosis in a subject comprising administering an aerosolized interferon-γ in a therapeutically effective amount.

19. The method of claim 18, wherein the tuberculosis improves as measured by an indication selected from the group consisting of a decrease in fever, a reduction in sputum production, a reduction in wheezing and a reduction in conversion of sputum cultures.

20. The method of claim 18, wherein the subject is unresponsive to treatment with one or more antibiotics.

21. The method of claim 18, wherein the tuberculosis is multiple drug resistant (MDR-TB).

22. The method of claim 18, wherein aerosolized interferon-γ is administered at a dose ranging from about 100 to 750 μg at least three times per week.

23. The method of claim 18, wherein aerosolized interferon-γ is administered as a dose of about 200 μg at least three times per week.

* * * * *